US008946682B2

(12) United States Patent
Goel et al.

(10) Patent No.: US 8,946,682 B2
(45) Date of Patent: Feb. 3, 2015

(54) DONOR-ACCEPTOR FLUORENE SCAFFOLDS: A PROCESS AND USES THEREOF

(75) Inventors: Atul Goel, Lucknow (IN); Sumit Chaurasia, Lucknow (IN); Vijay Kumar, Lucknow (IN); Sundar Manoharan, Kanpur (IN); R. S. Anand, Kanpur (IN)

(73) Assignee: Council of Scientific & Industrial Research, New Delhi (IN)

( * ) Notice: Subject to any disclaimer, the term of this patent is extended or adjusted under 35 U.S.C. 154(b) by 304 days.

(21) Appl. No.: 12/894,428

(22) Filed: Sep. 30, 2010

(65) Prior Publication Data
US 2011/0210315 A1    Sep. 1, 2011

Related U.S. Application Data

(63) Continuation-in-part of application No. PCT/IN2009/000215, filed on Mar. 31, 2009.

(30) Foreign Application Priority Data

Mar. 31, 2008  (IN) .............................. 838/DEL/2008

(51) Int. Cl.
*H01L 29/08* (2006.01)
*C07D 295/155* (2006.01)
(Continued)

(52) U.S. Cl.
CPC ........ *C07D 295/155* (2013.01); *C07D 207/327* (2013.01); *C07D 211/14* (2013.01);
(Continued)

(58) Field of Classification Search
USPC .......................................................... 257/40
See application file for complete search history.

(56) References Cited

U.S. PATENT DOCUMENTS 5,708,130 A    1/1998  Woo et al.
(Continued)

FOREIGN PATENT DOCUMENTS

CA    2253746 A1    12/1997
(Continued)

OTHER PUBLICATIONS

Chao Tang, Fluorene-substituted pyrenes—Novel pyrene derivatives as emitters in nondoped blue OLEDs, Organic Electronics 7 (2006) 155-162.*

(Continued)

*Primary Examiner* — Caleb Henry
(74) *Attorney, Agent, or Firm* — Ladas & Parry LLP

(57) ABSTRACT

The present invention relates to novel donor-acceptor fluorene compounds, which can be used as for the fabrication of electroluminescent devices, and a process of preparing said novel compounds. More particularly, the present invention relates to amine donor and nitrile/ester acceptor fluorenes, fluorenones their π-conjugated systems and related compounds, processes for preparing the said compounds including oxidation of fluorenes to corresponding fluorenones and their use in preparing organic electronic devices such as organic light emitting diodes (OLEDs), photovoltaic/solar cell, Field effect transistors and other useful electroluminescent devices. The compounds are prepared by reacting 2H-pyran-2-ones in isolated or rigid conformations with cyclic ketones containing methylene carbonyl moiety in the presence of a base in an organic solvent. The present invention also relates to a new concept and approach to overcome the problem of 'Green emission defect' in 9-unsubstituted fluorene-based organic light emitting diodes which occurs due to the conversion of fluorenes to fluorenones that show emission mainly in green-yellow region. In the present invention we have placed donor-acceptor substituents in such a way that donor-acceptor fluorenones show emission in the blue region (instead of green-yellow region) thus improving the blue color purity and overcoming the problem of green emission defect.

12 Claims, 15 Drawing Sheets

(51) Int. Cl.

| | | |
|---|---|---|
| *C07D 207/327* | (2006.01) | |
| *C07D 211/14* | (2006.01) | |
| *C07D 307/54* | (2006.01) | |
| *C07D 333/24* | (2006.01) | |
| *H01L 51/00* | (2006.01) | |

(52) U.S. Cl.
CPC ............ *C07D307/54* (2013.01); *C07D 333/24* (2013.01); *H01L 51/0058* (2013.01); *Y02E 10/549* (2013.01)
USPC ...... 257/40; 257/E51.024; 548/529; 546/203; 546/195

(56) References Cited

U.S. PATENT DOCUMENTS

| | | | |
|---|---|---|---|
| 5,807,974 A | 9/1998 | Kim et al. | |
| 5,814,244 A | 9/1998 | Kreuder et al. | |
| 5,876,864 A | 3/1999 | Kim et al. | |
| 5,900,327 A | 5/1999 | Pei et al. | |
| 5,962,631 A | 10/1999 | Woo et al. | |
| 6,066,426 A * | 5/2000 | Mott et al. | 430/58.2 |
| 6,140,004 A * | 10/2000 | Mott et al. | 430/132 |
| 6,162,824 A * | 12/2000 | Ognyanov et al. | 514/438 |
| 6,169,163 B1 | 1/2001 | Woo et al. | |
| 6,309,763 B1 | 10/2001 | Woo et al. | |
| 6,353,083 B1 | 3/2002 | Inbasekaran et al. | |
| 6,541,602 B1 | 4/2003 | Spreitzer et al. | |
| 6,605,373 B2 | 8/2003 | Woo et al. | |
| 6,653,438 B1 | 11/2003 | Spreitzer et al. | |
| 6,818,260 B2 * | 11/2004 | Farrand et al. | 428/1.1 |
| 6,835,513 B2 * | 12/2004 | Jubran et al. | 430/58.15 |
| 6,835,514 B2 * | 12/2004 | Jubran et al. | 430/58.45 |
| 6,838,193 B2 * | 1/2005 | Tao et al. | 428/690 |
| 6,864,025 B2 * | 3/2005 | Law et al. | 430/58.6 |
| 6,872,824 B2 * | 3/2005 | Wong et al. | 544/294 |
| 6,905,804 B2 * | 6/2005 | Law et al. | 430/58.45 |
| 6,908,783 B1 * | 6/2005 | Kuehl et al. | 438/99 |
| 6,955,869 B2 * | 10/2005 | Jubran et al. | 430/79 |
| 7,011,917 B2 * | 3/2006 | Jubran et al. | 430/72 |
| 7,063,928 B2 * | 6/2006 | Law et al. | 430/119.6 |
| 7,074,885 B2 | 7/2006 | Uckert et al. | |
| 7,118,839 B2 * | 10/2006 | Law et al. | 430/58.15 |
| 7,202,004 B2 * | 4/2007 | Law et al. | 430/119.6 |
| 7,241,513 B2 * | 7/2007 | Suzuki et al. | 428/690 |
| 7,329,722 B2 * | 2/2008 | Vaitkeviciene et al. | 528/423 |
| 7,358,014 B2 * | 4/2008 | Law et al. | 430/58.15 |
| 7,479,357 B2 * | 1/2009 | Law et al. | 430/58.15 |
| 7,501,216 B2 * | 3/2009 | Jubran et al. | 430/58.35 |
| 7,674,795 B2 * | 3/2010 | Mailliet et al. | 514/252.04 |
| 2002/0051895 A1 * | 5/2002 | Cho et al. | 428/690 |
| 2003/0207188 A1 * | 11/2003 | Jubran et al. | 430/58.15 |
| 2004/0147742 A1 * | 7/2004 | Wong et al. | 544/230 |
| 2004/0253389 A1 * | 12/2004 | Suzuki et al. | 428/1.1 |
| 2005/0221124 A1 * | 10/2005 | Hwang et al. | 428/690 |
| 2005/0236977 A1 * | 10/2005 | Yamada et al. | 313/504 |
| 2007/0051922 A1 * | 3/2007 | Nakatani et al. | 252/301.35 |
| 2007/0232841 A1 * | 10/2007 | Igawa et al. | 585/27 |
| 2008/0007161 A1 * | 1/2008 | Kamatani et al. | 313/504 |
| 2008/0093980 A1 * | 4/2008 | Stoessel et al. | 313/504 |
| 2008/0193796 A1 * | 8/2008 | Arakane et al. | 428/690 |

FOREIGN PATENT DOCUMENTS

| | | |
|---|---|---|
| EP | 0259229 A1 | 3/1988 |
| WO | 99/54385 A1 | 10/1999 |
| WO | 00/22027 A1 | 4/2000 |
| WO | 00/46321 A1 | 8/2000 |
| WO | 01/81294 A1 | 11/2001 |
| WO | 2004/085450 A2 | 10/2004 |

OTHER PUBLICATIONS

Ramendra Pratap, 2-Oxobenzo[h]chromene: a novel entry for the concise and efficient synthesis of indeno[1,2-c]phenanthrines, Tetrahedron Letters 48 (2007) 4379-4382.*

Kai Zhang, "Stable white electroluminescence from single fluorene-based copolymers: using fluorenone as the green fluorophore and an iridium complex as the red phosphor on the main chain", Journal of Materials Chemistry, 2008, 18, 291-298 | 291.*

International Search Report; mailed Jul. 9, 2010; Appln. PCT/IN2009/000215.

Jia Chen, et al; "Proteomics of buccal squamous cell carcinoma: The involvement of multiple pathways in tumorigenesis", Proteomics, vol. 4, pp. 2465-2475; Aug. 2004.

Haven Baker, et al; "Proteome-wide analysis of head and neck squamous cell carcinomas using laser-capture microdissection and tandem mass spectrometry", Oral Oncology, vol. 41, pp. 183-199; Feb. 2005.

Qing-Yu He, et al; "Identification of tumor-associated proteins in oral tongue squamous cell carcinoma by proteomics", Proteomics, vol. 4, Issue 1, pp. 271-278; Jan. 2004.

Jens Rauch, et al; "Allogenic antibody-mediated identification of head and neck cancer antigens", Biochemical and Biophysical Research Communications, vol. 323, pp. 156-162, Available online Aug. 27, 2004.

M. Roesch-ely, et al; "Proteomic analysis reveals successive aberrations in protein expression from healthy mucosa to invasive head and neck cancer", Oncogene, vol. 26, pp. 54-64; Published online Jul. 3, 2006.

Chao Tang, et al; "Fluorene-substituted pyrenes-Novel pyrene derivatives as emitters in nondoped blue OLEDs", Organic Electronics, vol. 7, pp. 155-162, Available online Jan. 25, 2006.

Ramendra Pratap, et al; "2-Oxobenzo[h]chromene: a novel entry for the concise and efficient synthesis of indeno[1,2-c]phenanthrenes", Tetrahedron Letters, vol. 48, pp. 4379-4382, Available online Apr. 22, 2007.

Kwang-Yol Kay, et al; "Electroluminescent Properties of Novel Fluorene Derivatives with Aromatic Amine Moieties", Molecular Crystals and Liquid Crystals; XP002473090; 1 page Abstract Only.

Freek J. M. Hoeben, et al; "About Supramolecular Assemblies of π-Conjugated Systems", Chemical Reviews, vol. 105, Issue 4,pp. 1491-1546; Publication Date (Web): Mar. 10, 2005.

Peter F.H. Schwab, et al; "Synthesis and Properties of Molecular Rods. 2, Zig-Zag Rods", Chemical Reviews, vol. 105, Issue 4, pp. 1197-1279; Publication Date (Web): Apr. 13, 2005.

Martin Kreyenschmidt, et al; "A New Soluble Poly(p-phenylene) with Tetrahydropyrene Repeating Units", Macromolecules; vol. 28, Issue 13, pp. 4577-4582; Jun. 1995.

Martin Grell, et al; "A Glass-Forming Conjugated Main-Chain Liquid Crystal Polymer for Polarized Electroluminescence Applications", Advanced Materials vol. 9, Issue 10, pp. 798-802; 1997; There is no exact date given when researched online only year of publication.

Masahiko Fukuda, et al; "Synthesis of Fusible and Soluble Conducting Polyfluorene Derivatives and Their Characteristics", Journal of Polymer Science: Part A: Polymer Chemistry, vol. 31, Issue 10, pp. 2465-2471; Article first published online: Sep. 1993.

S. Setayesh, et al; "Bridging the Gap between Polyfluorene and Ladder-Poly-p-phenylene: Synthesis and Characterization of Poly-2,8-indenofluorene", Macromolecules; vol. 33, Issue 6, pp. 2016-2020; Publication Date(Web): Mar. 3, 2000.

Chung-Chih Wu, et al; "Unusual Nondispersive Ambipolar Carrier Transport and High Electron Mobility in Amorphous Ter(9,9-diarylfluorene)s", Journal American Chemical Society, vol. 125, pp. 3710-3711; Published on Web Mar. 7, 2003.

J. Salbeck, et al; "Low molecular organic glasses for blue electroluminescence", Synthetic Metals, vol. 91, Issue 1-3; pp. 209-215; Dec. 1997.

Fernando Fungo, et al; "Electrogenerated Chemiluminescence. 81. Influence of Donor and Acceptor Substituents on the ECL of a Spirobifluorene-Bridged Bipolar System", The Journal of Physical Chemistry, vol. 109, Issue 17, pp. 3984-3989; May 5, 2005.

Chih-Long Chiang, et al; "Red-Emitting Fluorenes as Efficient Emitting Hosts for Non-Doped, Organic Red-Light-Emitting Diodes", Advanced Functional Materials, vol. 15, No. 2, Feb. 2005, pp. 231-238.

(56) References Cited

OTHER PUBLICATIONS

M.E. Itkis, et al; "Magneto-Opto-Electronic Bistability in a Phenalenyl-Based Neutral Radical", Science, vol. 296, May 24, 2002, pp. 1443-1445.
S.K. Pal, et al; "Synthesis, Structure and Physical Properties of the First One-Dimensional Phenalenyl-Based Neutral Radical Molecular Conductor", Journal American Chemistry Society, vol. 126, Issue 5, pp. 1478-1484, Publication Date(Web): Jan. 20, 2004.
Yonggang Wu, et al; "Synthesis of Extremely Stable Blue Light Emitting Poly(spirobifluorene)s with Suzuki Polycondensation", Organic Letters, vol. 6, No. 20, pp. 3485-3487; Published on the Web Aug. 31, 2004.
C.W. Tang, et al; "Organic Electroluminescent Diodes", Applied Physics Letters, vol. 51, Issue 12, Sep. 21, 1987, pp. 913-915.
Michael Cölle, et al; "Preparation and Characterization of Blue-Luminescent Tris(8-hydroxyquinoline) aluminum ($Alq_3$)", Advanced Functional Materials, vol. 13, No. 2, Feb. 2003, pp. 108-112.
Bo Chao Lin, et al; "Charge Transport Properties of Tris(8-hydroxyquinolinato)aluminum(III): Why it is an Electron Transporter", Journal of American Chemical Society, vol. 127, pp. 66-67, Published on Web Dec. 13, 2004.
Glenn P. Bartholomew, et al; "Bichromophoric Paracyclophanes: Models for Interchromophore Delocalization", Accounts of Chemical Research, vol. 34, No. 1, pp. 30-39; Published on Web Jan. 16, 2001.
Glenn P. Bartholomew, et al; "Two-Photon Absorption in Three-Dimensional Chromophores Based on [2.2]-Paracyclophane", Journal of American Chemical Society, vol. 126, pp. 11529-11542; Published on Web Aug. 24, 2004.
Klaus Mullen, et al; "Electron Materials: The Oligomer Approach", 26 pages © Wiley-VCH 1998, ISBN 3-527-29438-4, Book printed in Great Britain.
Leni Akcelrud; "Electroluminescent polymers", Progress in Polymer Science, vol. 28, Issue 12, pp. 875-962; Dec. 2003.
Jiu Yan Li, et al; "Substituent Effect to Prevent Autoxidation and Improve Spectral Stability in Blue Light-Emitting Polyfluorenes", Chemistry A European Journal, vol. 11, Issue 15; pp. 4450-4457; Jul. 18, 2005.
Ullrich Scherf, et al; "Semiconducting Polyfluorenes-Towards Reliable Structure-Property Relationships", Advanced Materials, vol. 14, No. 7, Apr. 4, 2002, pp. 477-487.
Lorenz Romaner, et al; "The Origin of Green Emission in Polyfluorene-Based Conjugated Polymers: On-Chain Defect Fluorescence", Advanced Functional Materials, vol. 13, No. 8, Aug. 2003, pp. 597-601.
Abhishek P. Kulkarni, et al; "Fluorenone-Containing Polyfluorenes and Oligofluorenes: Photophysics, Origin of the Green Emission and Efficient Green Electroluminescence", Journal Physical Chemical; B, vol. 108, pp. 8689-8701, Published on Web May 22, 2004.
Emil J.W. List, et al; "The Effect of Keto Defect Sites on the Emission Properties of Polyfluorene-Type Materials", Advanced Materials, vol. 14, No. 5, Mar. 4, 2002; pp. 374-378.
Sung Yong Cho, et al; "Polyfluorenes without Monoalkylfluorene Defects", Journal of American Chemical Society, vol. 129, pp. 11910-11911; Published on Web Sep. 7, 2007.
Chun Huang, et al; "Solution-Processable Polyphenylphenyl Dendron Bearing Molecules for Highly Efficient Blue Light-Emitting Diodes", Organic Letters, vol. 7, No. 3, pp. 391-394, Published on Web Jan. 7, 2005.
N.C Greenham, et al; "Efficient light-emitting diodes based on polymers with high electron affinities", Nature, vol. 365, Oct. 14, 1993; pp. 628-630.
S.C. Moratti, et al; "High Electron Affinity Polymers for LEDs", Synthetic Metals, vol. 71, Issues 1-3; pp. 2117-2120; Apr. 1995.
Chien-Jun Jack Wu, et al; "Preparation and photoluminescence of p-terphenyl derivatives containing cyano groups", Tetrahedron, vol. 61, pp. 4735-4741; Available online Mar. 24, 2005.
Chun Huang, et al; "Solution-Processable Polyphenylphenyl Dendron Bearing Molecules for Highly Efficient Blue Light-Emitting Diodes", Organic Letters, vol. 7, No. 3, pp. 391-394; Published on Web Jan. 7, 2005.

Sven K. Weber, et al; "Preferential Oxidative Addition in Suzuki Cross-Coupling Reactions Across One Fluorene Unit", Organic Letters, vol. 8, No. 18, pp. 4039-4041; Published on Web Aug. 10, 2006.
Takakazu Yamamoto, et al; "Preparation of π-Conjugated Poly(thiophene-2,5-diyl), Poly(p-phenylene), and Related Polymers Using Zerovalent Nickel Complexes. Linear Structure and Properties of the π-Conjugated Polymers", Macromolecules, vol. 25, Issue 4, pp. 1214-1223, Publication Date: Feb. 1, 1992.
Satoshi Amagi, et al; "Threshold sheath potential for the nucleation and growth of cubic boron nitride by inductively coupled plasma enhanced chemical-vapor deposition", Applied Physics Letters, vol. 7, No. 8, Feb. 24, 1997, pp. 946-948.
Bruce H. Lipshutz, et al; "Biaryls via Suzuki Cross-Couplings Catalyzed by Nickel on Charcoal", Tetrahedron, vol. 56, Issue 15, Apr. 7, 2000; pp. 2139-2144.
Dirk Marsitzky, et al; "Self-Encapsulation of Poly-2,7-fluorenes in a Dendrimer Matrix", Journal of the American Chemical Society, vol. 123, No. 29, Jul. 25, 2001, pp. 6965-6972.
Sepas Setayesh, et al; "Polyfluorenes with Polyphenylene Dendron Side Chains: Toward Non-Aggregating, Light-Emitting Polymers", Journal American Chemical Society, vol. 123, pp. 946-953, Published on Web Jan. 16, 2001.
Sang Ho Lee, et al; "Synthesis and Characterization of Oligo(9,9-dihexyl-2,7-fluorene ethynylene)s: For Application as Blue Light-Emitting Diode", Organic Letters, vol. 3, No. 13, pp. 2005-2007, Published on Web May 25, 2001.
Zixing Wang, et al; "Synthesis and Characterization of 9-(cycloheptatrienylidene)fluorene Derivatives: Acid-Triggered "Switch on" of Fluorophores", Organic Letters, vol. 7, No. 1, pp. 87-90; Published on Web Dec. 10, 2004.
Shun-ichi Murahashi, et al; "Ruthenium-Catalyzed Oxidation of Alkanes with tert-Butyl Hydroperoxide and Peracetic Acid", Journal Organic Chemicals, vol. 65, pp. 9186-9193; Published on Web Nov. 28, 2000.
Ahmad Shaabani, et al; "Solvent free permanganate oxidations", Tetrahedron Letters, vol. 42, Issue 34, Aug. 20, 2001, pp. 5833-5836.
Ahmad Shaabani, et al; "Selective oxidation of alkylarenes in dry media with potassium permanganate supported on montmorillonite K10", Tetrahedron Letters, vol. 43, Issue 29, Jul. 15, 2002, pp. 5165-5167.
Malek Nechab, et al; "New aerobic oxidation of benzylic compounds: efficient catalysis by N-hydroxy-3,4,5,6-tetraphenylphthalimide (NHTPPI) /CuCl under mild conditions and low catalyst loading", Chem. Communications, pp. 1500-1501, First published as an Advanced Article on the Web May 28, 2004.
Keigo Kamata, et al; "Efficient Heterogeneous Oxidation of Alkylarenes with Molecular Oxygen", Organic Letters, vol. 6, No. 20, pp. 3577-3580; Published on Web Sep. 3, 2004.
Guanyu Yang, et al; "Selective Organocatalytic of Hydrocarbons by Dioxygen Using Anthraquinones and N-Hydroxyphthalimade", Organic Letters, vol. 7, No. 2, pp. 263-266; Published on Web Dec. 17, 2004.
Hirotoshi Kawabata, et al; "Benzylic Oxygenation of Alkylarenes with Molecular Oxygen in the Presence of Activated Carbon", Tetrahedron Letters, vol. 45, Issue 28, Jul. 5, 2004, pp. 5457-5459.
Ajay Kumar Mandal et al; "A Versatile Aerobic Oxidation of Organic Compounds Catalyzed by Cobalt(II) Porphyrins", Tetrahedron, vol. 53, No. 22, pp. 7641-7648, Jun. 1997.
Bimal K. Banik, et al; "Benzylic Oxidation by Sodium Bismuthate in Acetic Acid: A Simple Method for the Synthesis of Polycyclic Aromatic Ketones", Tetrahedron Letters, vol. 39, Issue 40, Oct. 1, 1998, pp. 7247-7250.
Jatin K. Nagpal, et al; "Oral Cancer: Reviewing the Present Understanding of its Molecular Mechanism and Exploring the Future Directions for its Effective Management", Oral Oncology, vol. 39, No. 3, Apr. 2003, pp. 213-221.
V. Patel, et al; "New Approaches to the Understanding of the Molecular Basis of Oral Cancer", Critical Reviews in Oral Biology & Medicine, vol. 12, No. 1, pp. 55-63, Jan. 1, 2001.
H. Schliephake; "Prognostic relevance of molecular markers of oral cancer—A review", International Association of Oral and Maxillofacial Surgeons, vol. 32, No. 3, pp. 233-245; Jun. 2003.

\* cited by examiner

General Synthesis of various template T-1 to T-3

Synthesis of Template T-1

Synthesis of Template T-2

Synthesis of Template T-3

Oxidation of fluorenes to fluorenones

Compound 5

Compound 14

Compound 49

DONOR-ACCEPTOR FLUORENE SCAFFOLDS: A PROCESS AND USES THEREOF

FIELD OF INVENTION

The present invention relates to novel donor-acceptor fluorenes, fluorenones and their π-conjugated systems of the general formula I which can be used potentially in preparing electroluminescent devices, and a process of preparing said novel compounds. More particularly, the present invention, relates to amine donor and nitrile/ester acceptor fluorenes, fluorenones and their π-conjugated systems and related compounds, processes for preparing the said compounds including oxidation of fluorenes to fluorenones and their uses in preparing electronic devices such as organic light emitting diodes (OLEDs), photovoltaic/solar cell, field effect transistors and other useful electroluminescent devices. The present invention also relates to a new concept and approach to overcome the problem of 'Green emission defect' in 9-unsubstituted fluorene-based organic light emitting diodes which occurs due to the conversion of fluorenes to fluorenones that show emission mainly in green-yellow region.

The present invention more particularly relates to a compound of formula I:

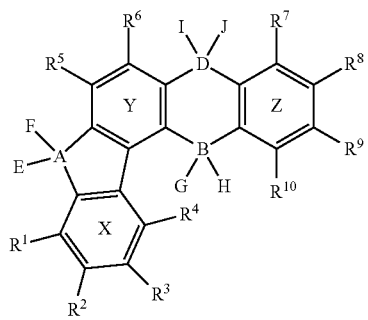

Wherein $R^1$, $R^2$, $R^3$, $R^4$, $R^5$, $R^6$, $R^7$, $R^8$, $R^9$, $R^{10}$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, nitriles, esters, hydroxy, mercapto, carbontrifluoride, nitro but not limited to this;

Wherein A, B, D is selected from the units consisting of one carbon or two carbons, optionally substituted one carbon unit or substituted two carbon units, optionally a ketone group, optionally substituted alkene, an oxygen atom, a sulfur atom, or a nitrogen atom;

Wherein in A, B, D units optionally either one unit is present, or optionally two units are present or optionally all three units are present, Wherein unit B or D may be nothing and bond is directly linked to aromatic Y-Z benzene ring;

Wherein units B, D and ring Z may not be present;

Wherein E, F, G, H, I, J is selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontifluoride, but not limited to this;

Wherein EF, GH or IJ together may be a double-bond directly linked to an oxygen atom or a methylene group or optionally substituted methylene-group;

BACKGROUND OF THE INVENTION

The development of efficient light emitting organic compounds for the fabrication of optoelectronic and electroluminescent materials such as organic light emitting diodes (OLEDs), solar cells, and field-effect transistors (FETs) has commanded increasing attention in recent years. The development of fluorescent blue-light emitting organic compounds for the fabrication of electroluminescent materials has been fascinating, challenging and hot research object of academic and industrial endeavours.[1] Various poly-acetylenes, poly-p-phenylenes, polyfluorenes, poly-heteroarenes and their cross-combination compounds with high luminescence quantum efficiencies have been developed.[2-5] However, the practical applicability of these first-generation π-conjugated compounds in preparing electroluminescent devices is restricted by their tendency to form aggregates and exciplexes leading to emission band broadening and bathochromic shift, thus exhibiting low quantum yield in the solid state. To alleviate their tendency to aggregate, nonplanar and/or asymmetric π-conjugated three-dimensional molecular hierarchies have been suggested, which may reduce the fluorescence quenching resulting from orbital interactions/overlapping through spatial proximity of π-groups. For this purpose, several tailor-made multiple t-conjugated molecular architectures such as spiro-(spirofluorenes),[6] ladder-(biphenalenes, phenylenes),[7] propeller-(metal-quinoline complex such as $Alq_3$),[8] and double-decker-type (p-cyclophanes)[9] monomers and polymers were synthesized.

Green Emission Defect:

Recently numerous tailor-made polyfluorenes or fluorenes with extended π-conjugated systems have proven their potential for preparing blue OLEDs with high quantum efficiencies[10], the scope of their commercialization suffers from the appearance of additional undesirable low-energy 'green emission' band during operation, covering a broad range from 500 to 600 nm, which destroys the blue color purity.[11]

The origin of 'green emission' band has been controversial and has not yet been fully understood.[11d] Initially it was believed that the origin of 'green emission' band was attributed to interchain aggregates and/or excimer formation, however no experimental observation[11c] supported the aggregates to be responsible for this low energy band. Instead, the experiments on fluorene-fluorenone systems suggest that the oxidation of fluorene to fluorenone is responsible for the emergence of this specific band. Researchers believe that such oxidation is possible either during polymerisation or by thermal-, photo-, or electrooxidation during device fabrication[11c] List et al[11e] proposed that highly active nickel ($Ni^0$) species used in the reductive coupling of 2,7-dihalofluorene in the synthesis of poly-2,7-fluorenes may initiate oxidation of fluorene units to fluorenones. Holmes et al.[11f] recently demonstrated that it is possible to prepare oxidatively stable polyfluorenes by carefully prefixing the dialkyl substitution at position 9 of fluorenes.

At the moment, the most challenging topic of realization is to understand the parameters and problem of 'green emission' defect, which we presume may be addressed by identifying the agents that trigger the oxidation of fluorene to fluorenones. Alternatively we have come up with a new concept/approach to overcome this defect by shifting the green emission band to the blue region through appropriate functionalization of donor-acceptor moieties on fluorene and fluorenone and related scaffolds. In the present invention we have placed donor-acceptor substituents in such a way that donor acceptor fluorenones show emission in the blue region (instead of green-yellow region) thus improving the blue colour purity and overcoming the problem of green emission defect.

Synthesis of Fluorene Scaffolds:

Fluorenes contain a rigid biphenyl structure locked into a coplanar arrangement by the presence of a methylene moiety. In general, palladium-catalyzed Suzuki-Miyaura coupling protocol has been used to prepare a wide array of fluorene, spirofluorenes and related scaffolds[12-14]. The use of nickel as a catalyst in coupling reactions for the synthesis of polyfluorenes has also been reported.[15] Despite the wide synthetic potential of these metal-assisted cross-coupling reactions, they suffer from the requirements for expensive organometallic reagents/catalysts, harsh reaction conditions, and undesired by-products. In addition, bulk production of these fluorenes for industrial purposes requires more investments for disposal of organometallic waste, purification of traces of metal impurities, and/or removal of by-products, from the final reaction mixture. Due to these limitations, in most of the reports, commercially available fluorene or 2,7-dihalofluorene has been used as a crucial precursor for preparing oligo- and polyfluorenes compromising with nonflexibility of introducing donor-acceptor substituents in their molecular scaffolds.[16] Therefore, developing simple, fast and general synthetic routes for fluorene and fluorenone structures is highly essential to further expanding the scope of applications of these rigid systems.

The present invention relates to a highly rapid novel synthesis of a new series of donor-acceptor fluorenes, fluorenones and their t-conjugated systems.

Oxidation of Fluorenes to Fluorenones:

Literature methodologies for the direct oxidation of fluorene to 9-fluorenone require specialized homogeneous or heterogeneous catalysts or harsh reaction conditions.[17] The present invention also relates to new highly rapid method for the oxidation of unsubstituted or substituted fluorenes to corresponding fluorenones by aerial oxidation without using any catalyst in the presence of a base such as metal hydrides or alkaline earth metal hydrides in an appropriate solvent such as THF at the temperature ranges from −30° C. to 25° C.

Some of related references and patents based on the present invention are mentioned below:

Selected References (1) (a) Marsitzky, D.; Mullen, K. In *Advances in Synthetic Metals, Twenty Years of Progress in Science and Technology*; Bernier, P., Lefrant, S., Bidan, G., Eds.; Elsevier. New York, 1999; p 1. (b) Krasovitskii, B. M.; Bolotin, B. M. In *Organic Luminescent Materials*; Vopian, V. G., VCH: Weinheim, Germany, 1988. (c) Valeur, B. In *Molecular Fluorescence*; Wiley-VCH: Weinheim, Germany, 2002.

(2) Reviews: (a) Hoeben, F. J. M.; Jonkheijm, P.; Meijer, E. W.; Schenning, A. P. H. J. *Chem. Rev.* 2005, 105, 1491-1546. (b) Schwab, P. F. H.; Smith, J. R.; Michl, *J. Chem. Rev.* 2005, 105, 1197-1279.

(3) Kreyenschmidt, M.; Uckert F.; Mullen, K. *Macromolecules* 1995, 28; 4577.

(4) (a) Grell, M.; Bradley, D. D. C.; Inbasekaran, M.; Woo, E. P. *Adv. Mater.* 1997, 9, 798. (b) Fukuda, M.; Sawada, K; Yoshino, K. *J. Polym. Sci. Polym. Chem.* 1993, 31, 2465.

(5) Setayesh, S.; Marsitzky, D.; Mullen, K. *Macromolecules* 2000; 33, 2016.

(6) (a) Wu, C.-C.; Liu, T.-L.; Hung, W.-L.; Hung, W.-Y.; Lin, Y.-T.; Wong, K.-T.; Chen, R.-T.; Chen, Y.-M.; Chien, Y.-Y. *J. Am. Chem. Soc.* 2003, 125, 3710. (b) Salbeck, J.; Yu, N.; Bauer, J.; Weissortel, F.; Bestgen, H. *Synth. Met.* 1997, 91, 209. (c) Fungo, F.; Wong, K.-T.; Ku, S.-Y.; Hung, Y.-Y.; Bard, A. J. *J. Phys. Chem. B* 2005, 109, 3984. (d) Chiang, C.-L.; Wu, M.-F.; Dai, D.-C.; Wen, Y.-S.; Wang, J.-K.; Chen, C.-T, *Adv. Funct. Mater.* 2005, 15, 231. (e) Itkis, M. E.; Chi, X; Cordes, A. W.; Haddon, R. C. *Science* 2002, 296, 1443. (f) Pal, S. K.; Itkis, M. E.; Reed, R. W.; Oakley, R. T.; Cordes, A. W.; Tham, F. S.; Siegrist, T.; Haddon, R. C. *J. Am. Chem. Soc.* 2004, 126, 1478. (g) Wu, Y.; Li, J.; Fu, Y.; Bo, Z. *Org. Lett.* 2004, 6, 3485.

(7) (a) Scherf, U.; Mullen, K. *Macromol. Chem., Rapid Commun.* 1991, 12, 489. (b) Muller, M.; Morgenroth, F.; Scherf, U.; Soczka-Guth, T.; Klaner, G.; Mullen, K. *Phil. Trans. R. Soc. Lond. A* 1997, 355, 715-726.

(8) (a) Tang, C. W.; VanSlyke, S. A. *Appl. Phys. Lett.* 4987, 51, 913. (b) Colle, M.; Gmeiner, J.; Milius, W.; Hillebrecht, H.; Brutting, W. *Adv. Funct. Mater.* 2004, 13, 108. (c) Lin, B. C.; Cheng, C. P.; You, Z.-Q.; Hsu, C.-P. *J. Am. Chem. Soc.* 2005, 127, 66.

(9) (a) Bartholomew, G. P.; Bazan, G. C. *Acc. Chem. Res.* 2001, 34, 30. (b) Bartholomew, G. P.; Rumi, M.; Pond, S. J. K.; Perry, J. W.; Tretiak, S.; Bazan, G. C. *J. Am. Chem. Soc.* 2004, 126, 11529.

(10) (a) Mullen, K.; Wegner, G. *Electronic Materials: The Oligomer Approach*; Wiley-VCH: Weinheim, N.Y., 1998. (b) Miyata, S.; Nalwa, H. S. *Organic Electroluminescent Materials and Devices*; Gordon and Breach Publishers: Amsterdam, 1997. (c) Akcelrud, L. *Prog. Polym. Sci* 2003, 28, 875-962.

(11) (a) Li, J. Y.; Ziegler, A.; Wegner, G. *Chem. Eur. J.* 2005, 11, 4450-445-7 and references cited: therein. (b) Scherf, U; List, E. J. W. *Adv. Mater.* 2002, 14, 477-487. (c) Romaner, L.; Pogantsch; A.; de Freitas, P. S.; Scherf; U; Gaal, M.; Zojer, E.; List, E. J. W. *Adv. Funct. Mater.* 2003, 13, 597-601. (d) Kulkarni, A. P.; Kong, X.; Jenekhe, S. A. *J. Phys. Chem. B* 2004, 108, 8689-8701. (e) List, E. J. W.; Guentner, R.; de Freitas, P. S.; Scherf, U. *Adv. Mater.* 2002, 14, 374-378. (f) Cho, S. Y.; Grimsdale, A. C.; Jones, D. J.; Watkins, S. E.; Holmes, A. B. *J. Am. Chem. Soc.* 2007, 129, 11910.

(12) Huang, C.; Zhen, C.-G.; Su, S. P.; Loh, K. P.; Chen, Z.-K. *Org. Lett.* 2005, 7, 391-394.

(13) (a) Greenham, N. C.; Moratti, S. C.; Bradley, D. D. C.; Friend, R. H.; Holmes, A. B. *Nature* 1993, 365, 628. (b) Moratti, S. C.; Cervini, R.; Holmes, A. B.; Baigent, D. R.; Friend, R. H.; Greenham, N. C.; Griuner, J.; Hamer, P. J. *Synth. Met.* 1995, 71, 2117. (c) Wu, C.-J. J.; Xue, C.; Kuo, Y.-M.; Luo, F.-T. *Tetrahedron* 2005, 61, 4735. (d) Wang, Z.; Zheng, G.; Lu, P. *Org. Lett.* 2005, 7, 391.

(14) (a) Wu, Y.; Li, T.; Fu, Y.; Bo, Z. *Org. Lett.* 2004; 6, 3485-3487. (b) Weber, S. K.; Galbrecht, F.; Scherf, U. *Org. Lett.* 2006, 8, 4039-4041.

(15)(a) Yamamoto, T.; Morita, A.; Muyazaki, Y.; Maruyama, T.; Wakayama, H.; Zhou, Z.-H.; Nakamura, Y.; Kanbara, T.; Sasaki, S.; Kubota, K. *Macromolecules* 1992, 25, 1214-23. (b) Yang, Y.; Pei, Q. *Appl Phys Lett* 1997, 81, 3294-8. (c) Lipshutz, B. H.; Sclafani, J. A.; Blomgren, P. A. *Tetrahedron* 2000, 56, 2139-44.

(16) (a) Marsitzky, D.; Vestberg, R.; Blainey, P.; Tang, B. T.; Hawker, C. J.; Carter, K. R. *J. Am. Chem. Soc.* 2001, 123, 6965. (b) Setayesh, S.; Grimsdale, A. C.; Well, T.; Enkelmann, V.; Mullen, K I C; Meghdadi, F.; List, E. J. W.; Leising, G. *J. Am. Chem. Soc.* 2001, 123, 946-953. (c) Lee, S. H.; Nakamura, T.; Tsutsui, T. *Org. Lett* 2001, 3, 2005-2007. (d) Wang, Z.; Xing, Y.; Shao, H.; Lu, P.; Weber, W. P. *Org. Lett.* 2005, 7, 87-90.

(17) (a) S.-I. Murahashi, N. Komiya, Y. Oda, T. Kuwabara, T. Naota *J. Org. Chem.* 2000, 65, 9186-9193. (b) A. Shaabani, D. G. Lee *Tetrahedron Lett.* 2001, 42, 5833-5836. (c) A. Shaabani, A. Bazgir, F. Teimouri, D. G. Lee *Tetrahedron Lett.* 2002, 43, 5165-5167. (d) R. Badri, M. Soleymani *Syn. Commun.* 2002, 32, 2385-2389. (e) M. Neehab, C. Einhorn, J. Einhorn, *Chem. Commun.* 2004, 1500-1501. (f) K. Kamata, J. Kasai, K. Yamaguchi, N. Mizuno, *Org. Lett.* 2004, 6, 3577-3580. (g) G. Yang, Q. Zhang, H. Miao, X. Tong, J. Xu *Org. Lett.* 2005, 7, 263-266. (h) H. Kawabata, M. Hayashi *Tetrahedron Lett.* 2004, 45, 5457-5459. (i) A. K. Mandal, J. Iqbal *Tetrahedron* 1997, 53, 7641-7648. (j) Y. Ishii, K. Nakayama, M. Takeno, S. Sakaguchi, T. Iwahama, Y. Nishiyama *J. Org. Chem.* 1995, 60, 3934-3935. (k) B. K. Banik, M. S. Venkatraman, C. Mukhopadhyay, F. F. Becker *Tetrahedron Lett.* 1998, 39, 7247-7250. (l) patent:

Selected U.S. Patent in this Field of Invention

Another object of the invention is to provide a process for the preparation of the novel donor-acceptor fluorenes, fluorenones and their n-conjugated compounds having the general formula I.

Another object of the invention is to provide a process for the oxidation of the novel donor-acceptor fluorenes to novel donor-acceptor fluorenones having the general formula I.

Further object of the invention is to provide the compounds having the general formula I which are useful in preparing electronic devices such as organic light emitting diodes (OLEDs), photovoltaic/solar cell, Field effect transistors and other useful electroluminescent devices.

Another object of the present invention relates to overcome the problem of 'green emission defect' caused by oxidation of 9-unsubstituted-fluorene units in oligofluorenes or polyfluorenes into corresponding fluorenones, which show green emission band and destroys the purity of blue color polyfluorene based OLEDs.

SUMMARY OF THE INVENTION

The present invention relates to novel donor-acceptor fluorenes, fluoreneones and π-conjugated compounds, which can be used for the fabrication of electroluminescent devices, and a process of preparing said novel compounds. More particularly, the present invention relates to amine donor and nitrile/ester acceptor fluorenes, fluorenones and their π-conjugated

| | | |
|---|---|---|
| 5,708,130 | January, 1998 | 2,7-aryl-9-substituted fluorenes and 9-substituted fluorene oligomers and polymers |
| 5,807,974 | September, 1998 | Fluorene-based alternating copolymers for electroluminescence element and electroluminescence element using such copolymers as light emitting materials |
| 5,814,244 | September, 1998 | Polymers comprising triaylamine units as electroluminescence materials |
| 5,876,864 | March, 1999 | Fluorene-based alternating polymers containing acetylene group and electroluminescence element using the same |
| 5,900,327 | May, 1999 | Polyfluorenes as materials for photoluminescence and electroluminescence |
| 5,962,631 | October, 1999 | 2,7-aryl-9-substituted fluorenes and 9-substituted fluorene oligomers and polymers |
| 6,169,163 | January, 2001 | Fluorene-containing polymers and compounds useful in the preparation thereof |
| 6,309,763 | October, 2001 | Fluorene-containing polymers and electroluminescent devices therefrom |
| 6,353,083 | March, 2002 | Fluorene copolymers and devices made therefrom |
| 6,541,602 | April, 2003 | Conjugated polymers containing 2,7 fluorenyl units with improved properties |
| 6,605,373 | August, 2003 | Fluorene-containing polymers and electroluminescent devices therefrom |
| 6,653,438 | November, 2003 | Conjugated polymers containing special fluorene structural elements with improved properties |
| 7,074,885 | February 2002 | Electroactive fluorene copolymers and devices made with such polymers |
| EP0259229 | September, 1987 | 9,9'-Disubstituted polyfluorenes, process for their preparation and their use in electro-optics and electrochemistry. |
| CIPO 02253746 | Oct. 6, 1998 | Process for making fluorenones |
| WO/2000/022027 | April, 2000 | Conjugated polymers containing 2,7 fluorenyl units with improved properties |
| WO/2000/046321 | August, 2000 | Fluorene copolymers and devices made therefrom |
| WO/2001/081294 | November, 2001 | End-capped polyfluorenes, films and devices based thereon |
| WO/1999/054385 | October, 1999 | Fluorene-containing polymers and electroluminescent devices therefrom |

Objects of the Invention

Main object of the present invention is to provide novel donor-acceptor fluorenes, fluoreneones and π-conjugated compounds having the general formula I.

systems and related compounds, processes for preparing the said compounds and their use in preparing organic electronic devices such as organic light emitting diodes (OLEDs), photovoltaic/solar cell, Field effect transistors and other useful electroluminescent devices. The compounds are prepared by reacting 2H-pyran-2-ones in isolated or rigid conformations with cyclic ketones containing methylene carbonyl moiety in the presence of a base in an organic solvent. The present invention also provides a process for the oxidation of the novel donor-acceptor fluorenes and related diarylmethane compounds to corresponding novel donor-acceptor fluorenones or diarylcarbonyl compounds. The present invention also provides a possible solution to overcome the problem of 'green emission defect' caused by oxidation of 9-unsubstituted-fluorene units in reported fluorenes, oligofluorenes or polyfluorenes into corresponding fluorenones, which show green emission band and destroys the purity of blue color OLEDs.

BRIEF DESCRIPTION OF THE DRAWINGS

The present invention may be more clearly understood by reference to the following Table/Figures.

Table 1 represents the photo physical properties of the compounds of the invention.

DETAILED DESCRIPTION

Figure 1:
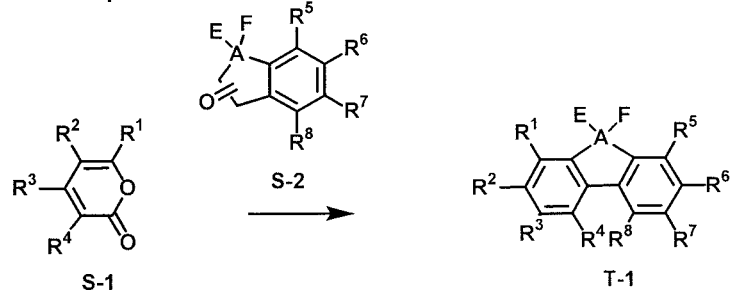
FIG. 1 illustrates the reaction sequence (Schemes 1-3) resulting in the preparation of various fluorene derivatives and related scaffolds.
Figure 1:
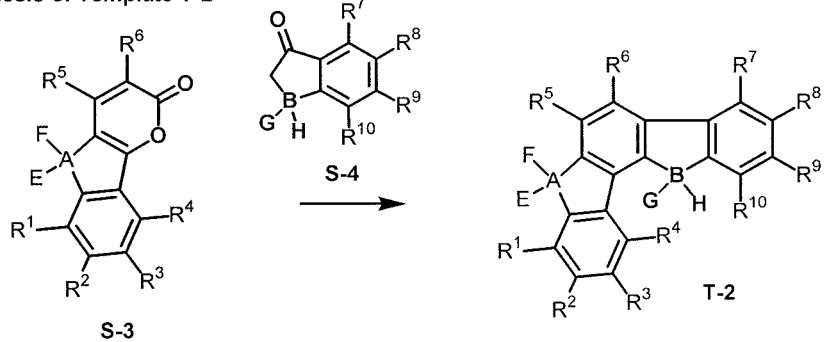
Figure 1:
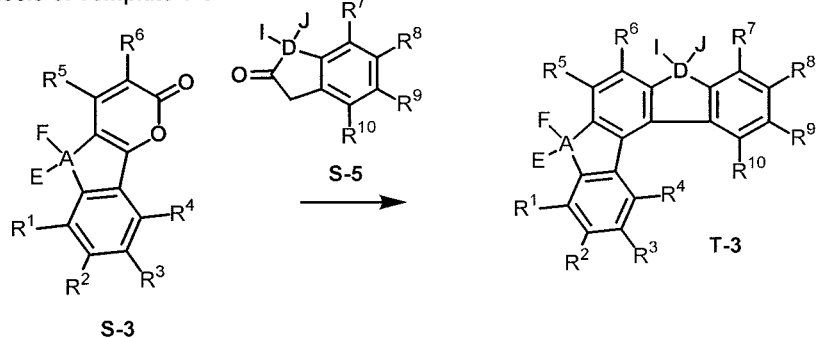
Figure 2:
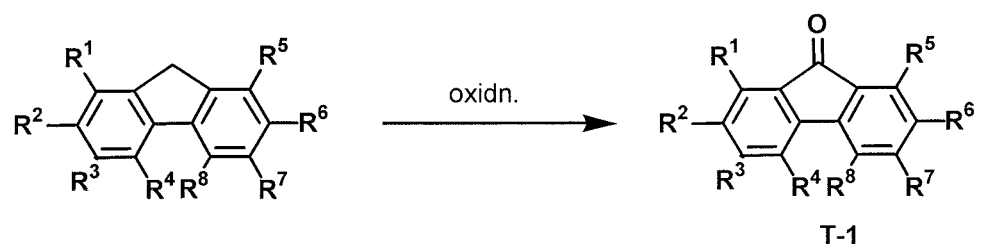
FIG. 2 illustrates the reaction sequence resulting in the oxidation of various fluorene derivatives and related scaffolds to corresponding fluorenones.
Figure 3:
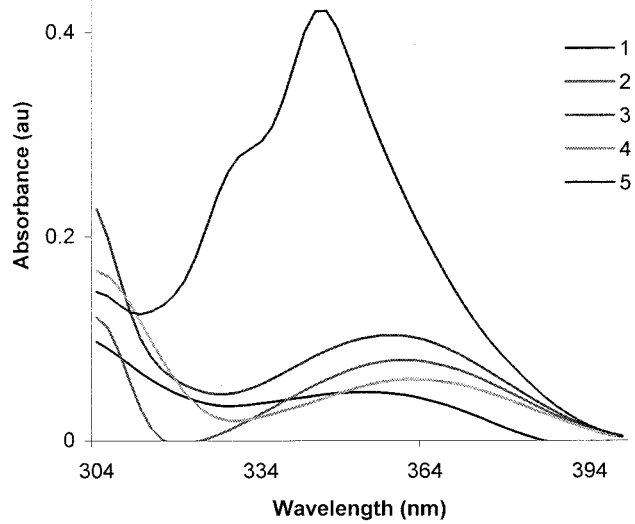
FIG. 3 illustrates UV spectra of selected compounds.
Figure 3:
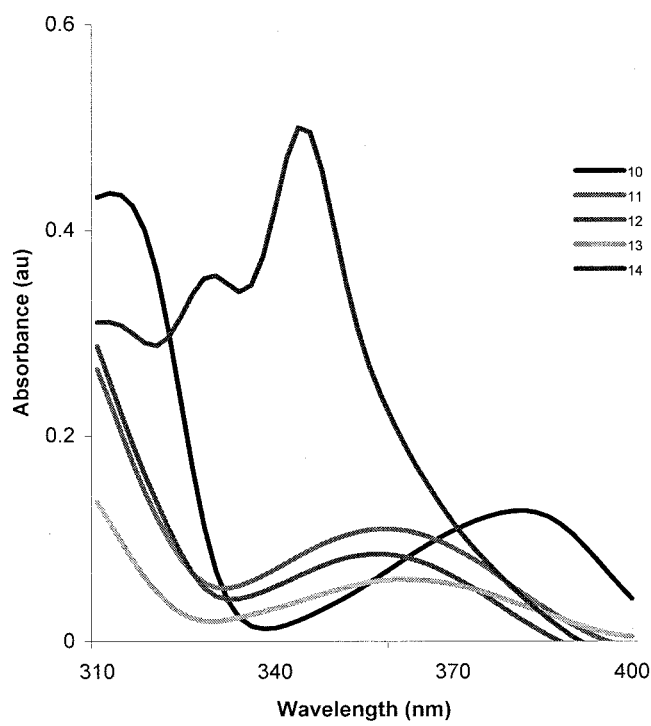
Figure 3:
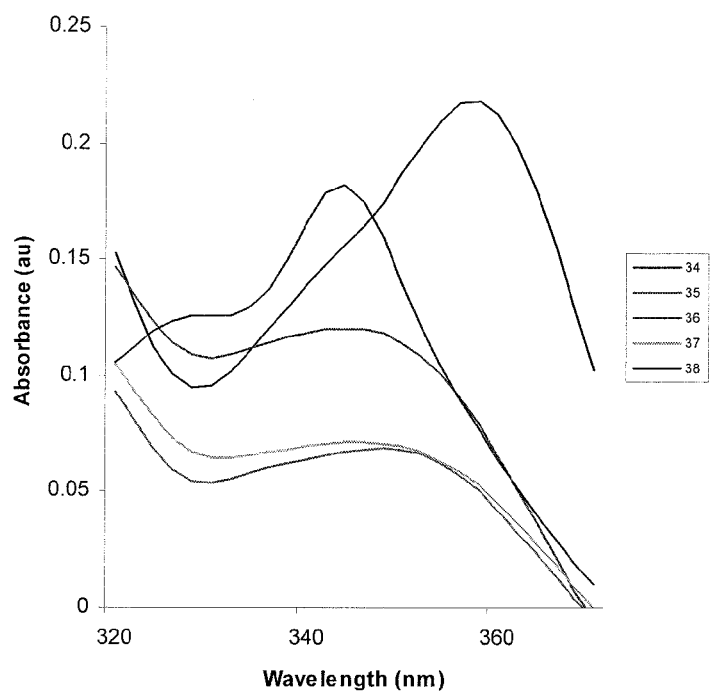
Figure 3:
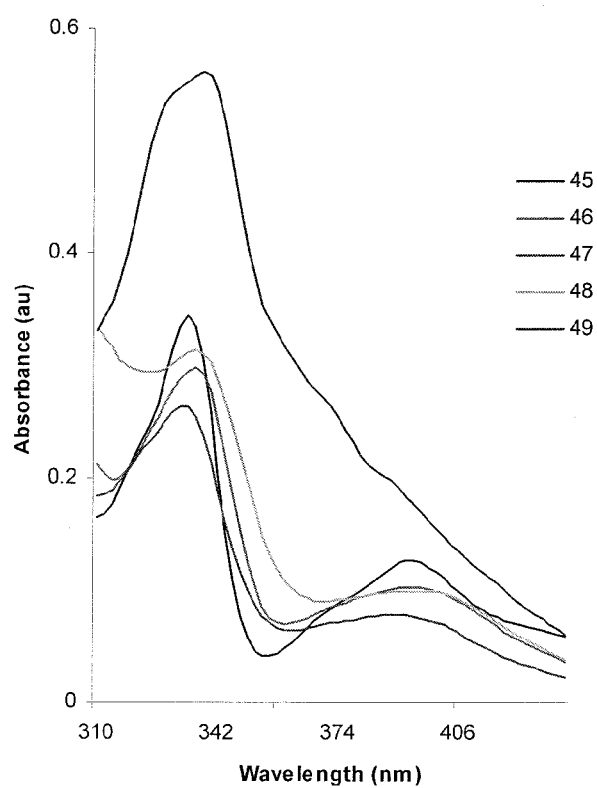
Figure 4:
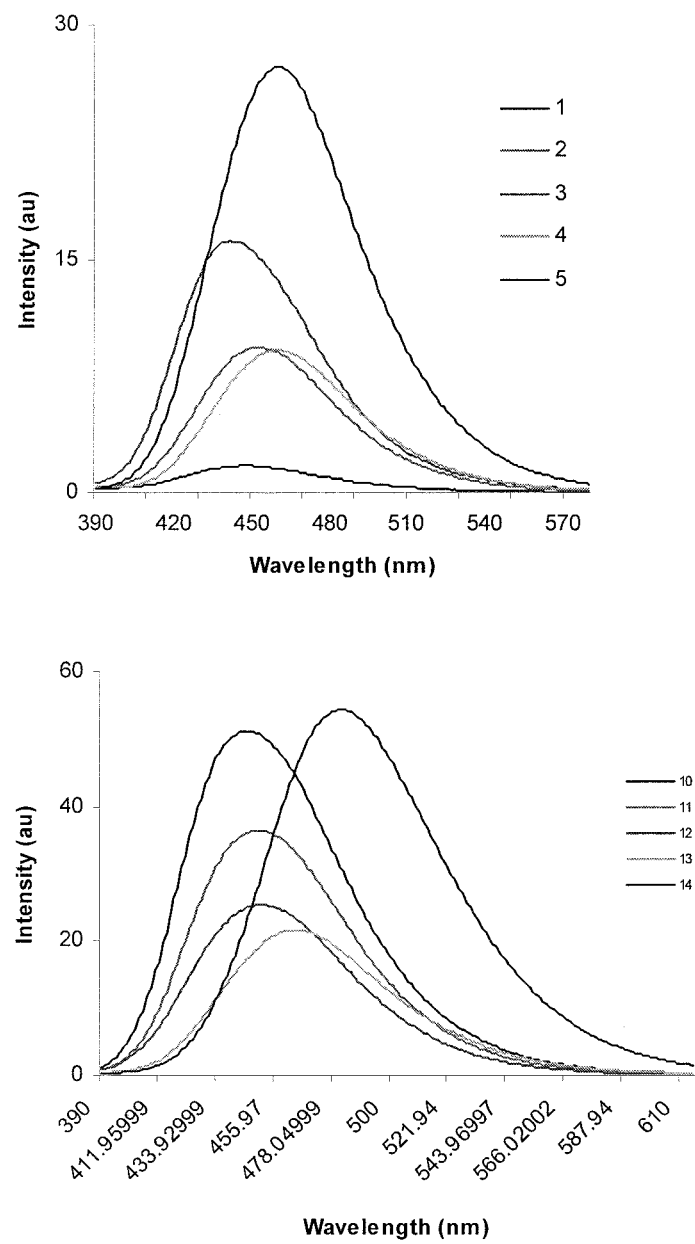
FIG. 4 illustrates fluorescence spectra of selected compounds.
Figure 4:
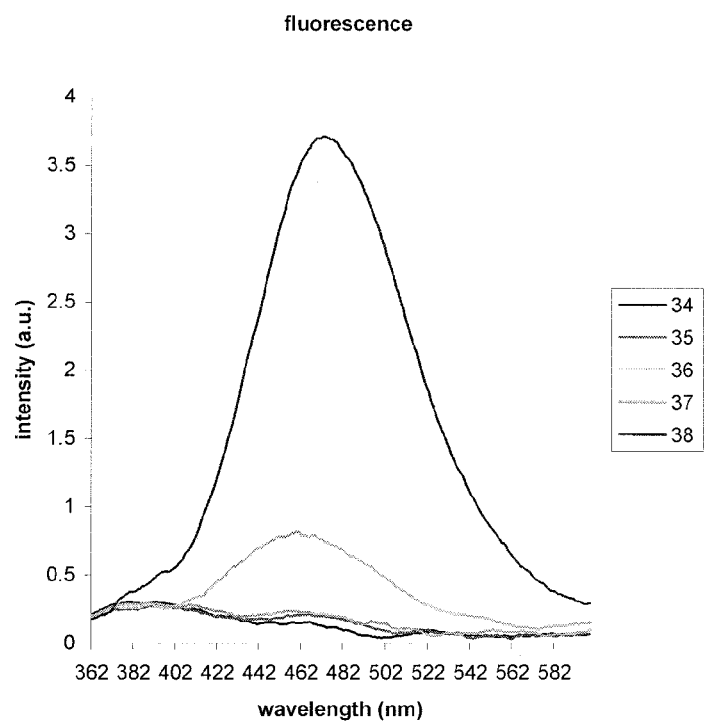
Figure 4:
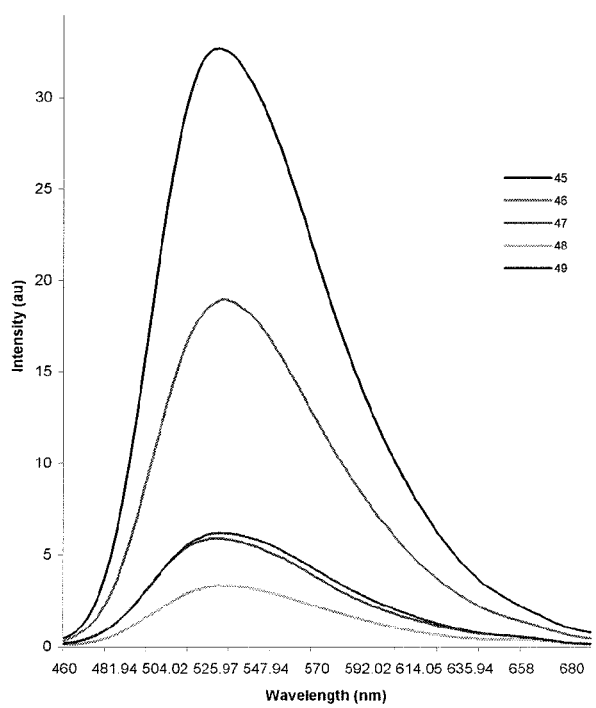

Accordingly, the present invention provides a novel donor-acceptor fluorenes, fluorenones and their π-conjugated scaffolds having the general formula I, and derivatives thereof

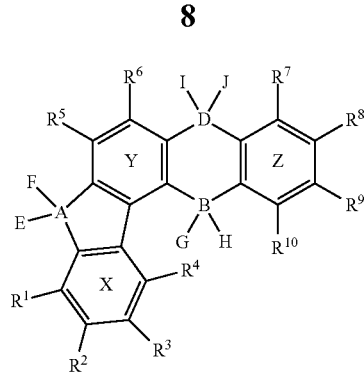

Wherein $R^1, R^2, R^3, R^4, R^5, R^6, R^7, R^8, R^9, R^{10}$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, nitriles, esters, hydroxy, mercapto, carbontrifluoride, nitro;

Wherein A, B, D is selected from the units consisting of one carbon or two carbons, optionally substituted one carbon unit or substituted two carbon units, optionally a ketone group, optionally substituted alkene, an oxygen atom, a sulfur atom, or a nitrogen atom;

Wherein in A, B, D units optionally either one unit is present, or optionally two units are present or optionally all three units are present, Wherein unit B or D may be nothing and bond is directly linked to aromatic Y-Z benzene ring;

Wherein units B, D and ring Z may not be present;

Wherein E, F, G, H, I, J is selected from the groups consisting of hydrogen, optionally substituted alkyl, optionally substituted alkenyl, optionally substituted alkoxyl, optionally substituted aryl optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro.

Wherein EF, GH or IJ together may be a double bond directly linked to an oxygen atom or a methylene group or optionally substituted methylene group;

In an embodiment of the invention wherein the especially-preferred compounds having the general formula I are more specifically described by Templates T-1 to T-3 with the proviso that at least one donor group such as substituted or unsubstituted amino and one acceptor group such as nitrile, ester functionality is present on these scaffolds;

T-1

-continued

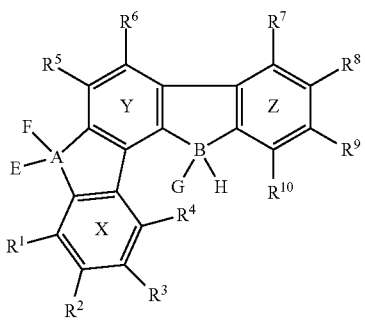

T-2

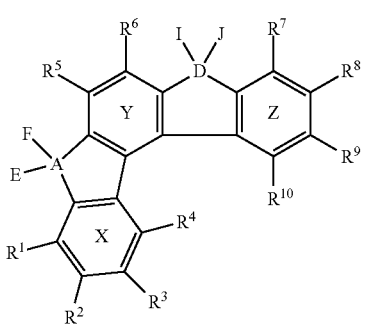

T-3

Wherein in Template T-1, $R^1$, $R^2$, $R^3$, $R^4$, $R^5$, $R^6$, $R^7$, $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro;

Wherein in Template T-1, A is selected from the units consisting of optionally substituted or unsubstituted one carbon unit, optionally a ketone group, optionally substituted alkene, an oxygen atom, a sulfur atom, or a nitrogen atom;

Wherein in Template T-1, E and/or F is selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, caibontrifluoride, nitro.

Wherein in Template T-1, EF together may be a double bond directly linked to an oxygen atom or a methylene group or optionally substituted methylene group;

Wherein in Template T-2, $R^1$, $R^2$, $R^3$, $R^4$, $R^5$, $R^6$, $R^7$, $R^8$, $R^9$, $R^{10}$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro;

Wherein in Template T-2, A and B is selected from the units consisting of one carbon or two carbons, optionally substituted one carbon unit or substituted two carbon units, optionally a ketone group, optionally substituted alkene, an oxygen atom, a sulfur atom, or a nitrogen atom;

Wherein in Template T-2, E, F, G, H is selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro.

Wherein in Template T-2, EF and/or GH together may be a double bond directly linked to an oxygen atom or a methylene group or optionally substituted methylene group;

Wherein in Template T-3, $R^1$, $R^2$, $R^3$, $R^4$, $R^5$, $R^6$, $R^7$, $R^8$, $R^9$, $R^{10}$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro;

Wherein in Template T-3, A and D is selected from the units consisting of one carbon or two carbons, optionally substituted one carbon unit or substituted two carbon units, optionally a ketone group, optionally substituted alkene, an oxygen atom, a sulfur atom, or a nitrogen atom;

Wherein in Template T-3, E, F, I, J is selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro;

Wherein in Template T-3, EF and/or IJ together may be a double bond directly linked to an oxygen atom or a methylene group or optionally substituted methylene group.

In another embodiment of the invention wherein donor groups may be selected from a group consisting of amine such as pyrrolidine, piperidine, methyl amine, ethyl amine, propyl amine, dimethylamine but not limited to this.

In yet another embodiment of the invention wherein acceptor group may be selected from a group consisting of nitrile, esters but not limited to this In another embodiment of the invention wherein the representative compounds comprising;
1) 1-Phenyl-3-pyrrolidin-1-yl-9H-fluorene-4-carbonitrile
2) 1-Phenyl-3-piperidin-1-yl-9H-fluorene-4-carbonitrile
3) 1-Naphthalen-1-yl-3-piperidin-1-yl-9H-fluorene-4-carbonitrile
4) 1-Naphthalen-2-yl-3-piperidin-1-yl-9H-fluorene-4-carbonitrile
5) 3-Piperidin-1-yl-1-pyren-1-yl-9H-fluorene-4-carbonitrile
6) 3,5-Dimethyl-furan-2-yl)-3-piperidin-1-yl-9H-fluorene-4-carbonitrile
7) 1-(4-Fluoro-phenyl)-3-piperidin-1-yl-9H-fluorene-4-carbonitrile 8) 3-Piperidin-1-yl-1-thiophen-2-yl-9H-fluorene-4-carbonitrile
9). 4-Furan-2-yl-2-piperidin-1-yl-9H-fluorene-1-carbonitrile
10) 4-Phenyl-2-pyrrolidin-1-yl-9H-fluorene-1-carbonitrile
11) 4-Phenyl-2-piperidin-1-yl-9H-fluorene-1-carbonitrile
12) 4-Naphthalen-1-yl-2-piperidin-1-yl-9H-fluorene-1-carbonitrile
13) 4-Naphthalen-2-yl-2-piperidin-1-yl-9H-fluorene-1-carbonitrile
14) 2-Piperidin-1-yl-4-pyren-1-yl-9H-fluorene-1-carbonitrile
15) 4-(4-Methoxy-phenyl)-2-piperidin-1-yl-9H-fluorene-1-carbonitrile
16) 2-Piperidin-1-yl-4-p-tolyl-9H-fluorene-1-carbonitrile:
17) 4-(4-Chloro-phenyl)-2-pyrrolidin-1-yl-9H-fluorene-1-carbonitrile
18) 2-Pyrrolidin-1-yl-4-p-tolyl-9H-fluorene-1-carbonitrile
19) 2-Piperidin-1-yl-4-thiophen-2-yl-9H-fluorene-1-carbonitrile
20) 2-Piperidin-1-yl-4-(4-pyrrol-1-yl-phenyl)-9H-fluorene-1-carbonitrile
21) 4-(4-Acetyl-phenyl)-2-piperidin-1-yl-9H-fluorene-1-carbonitrile
22) 4-(4-Fluoro-phenyl)-2-piperidin-1-yl-9H-fluorene-1-carbonitrile
23) 4-(4-Bromo-phenyl)-2-piperidin-1-yl-9H-fluorene-1-carbonitrile
24) 6-Piperidin-1-yl-7,12-dihydro-indeno[1,2-a]fluorene-5-carbonitrile
25) 6-Pyrrolidin-1-yl-7,12-dihydro-indeno[1,2-a]fluorene-5-carbonitrile
26) 3-Methoxy-6-piperidin-1-yl-7,12-dihydro-indeno[1,2-a]fluorene-5-carbonitrile
27) 7-Piperidin-1-yl-5,8-dihydro-indeno[2,1-c]fluorene-6-carbonitrile
28) 7-Pyrrolidin-1-yl-5,8-dihydro-indeno[2,1-c]fluorene-6-carbonitrle
29) (4-Methyl-piperidin-1-yl)-5,8-dihydro-indeno[2,1-c]fluorene-6-carbonitrile
30) 11-Methoxy-7-piperidin-1-yl-5,8-dihydro-indeno[2,1-c]fluorene-6-carbonitrile
31) 7-Piperidin 1-yl-5,9-dihydro-6H-indeno[2,1-c]phenanthrene-8-carbonitrile
32) 7-Pyrrolidin-1-yl-5,9-dihydro-6H-indeno[2,1-c]phenanthrene-8-carbonitrile
33) 7-(4-Methyl-piperidin-1-yl)-5,9-dihydro-6H-indeno[2,1-c]phenanthrene-8-carbonitrile
34) 9-Oxo-4-phenyl-2-pyrrolidin-1-yl-9H-fluorene-1-carbonitrile
35) 9-Oxo-4-phenyl-2-piperidin-1-yl-9H-fluorene-1-carbonitrile
36) 4-Naphthalen-1-yl-9-oxo-2-piperidin-1-yl-9H-fluorene-1-carbonitrile
37) 4-Naphthalen-2-yl-9-oxo-2-piperidin-1-yl-9H-fluorene-1-carbonitrile
38) 9-Oxo-2-piperidin-1-yl-4-pyren-1-yl-9H-fluorene-1-carbonitrile
39) 9-Oxo-2-piperidin-1-yl-4-thiophen-2-yl-9H-fluorene-1-carbonitrile
40) 4-Furan-2-yl-2-piperidin-1-yl-9H-fluorene-1-carbonitrile
41) 4-(4-Methoxy-phenyl)-9-oxo-2-piperidin-1-yl-9H-fluorene-1-carbonitrile
42) 4-(4-Fluoro-phenyl) 9-oxo-2-piperidin-1-yl-9H-fluorene-1-carbonitrile
43) 9-Oxo-2-piperidin-1-yl-4-p-tolyl-9H-fluorene-1-carbonitrile
44) 9-Oxo-2-pyrrolidin-1-yl-4-p-tolyl-9H-fluorene-1-carbonitrile
45) 9-Oxo-1-phenyl-3-pyrrolidin-1-yl-9H-fluorene-4-carbonitrile
46) 9-Oxo-1-phenyl-3-piperidin-1-yl-9H-fluorene-4-carbonitrile
47) 1-Naphthalen-1-yl-9-oxo-3-piperidin-1-yl-9H-fluorene-4-carbonitrile
48) 1-Naphthalen-2-yl-9-oxo-3-piperidin-1-yl-9H-fluorene-4-carbonitrile
49) 9-Oxo-3-piperidin-1-yl-1-pyren-1-yl-9H-fluorene-4-carbonitrile
50) 9-Oxo-3-piperidin-1-yl-1-thiophen-2-yl-9H-fluorene-4-carbonitrile
51) 1-(4-Fluoro-phenyl)-9-oxo-3-piperidin-1-yl-9H-fluorene-4-carbonitrile Accordingly the present invention provides a process for the preparation of novel fluorenes, fluorenones and their π-conjugated scaffolds of the general formula I comprising template T-1 or template T-2 or template T-3;

Wherein the present invention provides a process for the preparation of novel compounds having the general formula T-1 as shown in drawing accompanying the specification represents a preferred embodiment of this process for the compounds from template T-1:

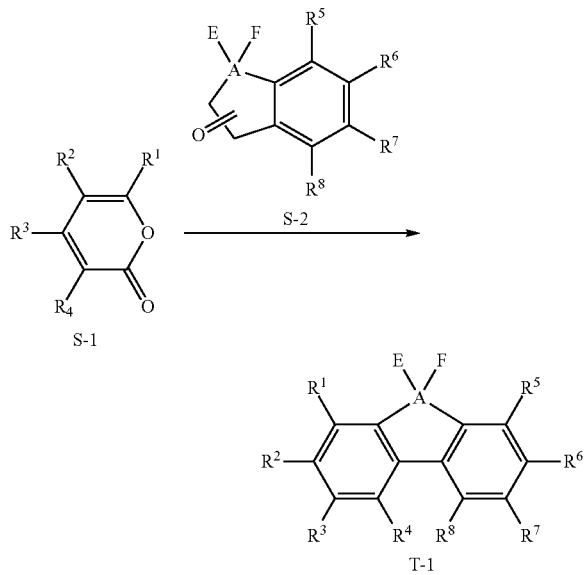

Synthesis of Template T-1 a) reacting a compound having general formula S-1 with a compound having general formula S-2 to furnish a compound having the general formula T-1 wherein $R^1$, $R^2$, $R^3$, $R^4$, $R^5$, $R^6$, $R^7$, $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro;

Wherein, A is selected from the units consisting of optionally substituted or unsubstituted one carbon unit, optionally a ketone group, optionally substituted alkene, an oxygen atom, a sulfur atom, or a nitrogen atom;

Wherein, E and/or F is selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted, acylthio, optionally substituted acyl, optionally substituted aroyl, optionally substituted acyloxy, optionally substituted thioamido, halogens, esters, hydroxy, mercapto, carbontrifluoride, nitro;

Wherein, EF together may be a double bond directly linked to an oxygen atom or a methylene group or optionally substituted methylene group;

b) wherein in step a, reaction may proceeds in a common organic solvent particularly DMF, THF (but not limited to this) in the presence of a base particularly KOH, NaH, KH (but not limited to this) at a temperature ranging between −78° C. to 100° C. for a period ranging between <1 minute to 24 hr, c) wherein, isolating the compound of general formula T-1 from the reaction mixture obtained in step a and purifying by chromatographic techniques;

d) The starting material of the general formula S-1 and S-2 are known and the compound of the general formula S-1 has been prepared by the action of methyl 2-cyano/methoxycarbonyl-3,3-di(methylsulfanyl)acrylate with substituted acetophenones under alkaline conditions in dry DMSO in high yields according to the procedure reported earlier [(a) Tominaga, Y.; Ushirogouchi, A.; Matsuda, Y.; Kobayashi, G. *Chem. Pharm. Bull.* 1984; 32, 3384. (b) Tominaga, Y.; Ushirogouchi, A.; Matsuda, Y. *J. Heterocycl. Chem.* 1987, 24, 1557. (c) Farhanullah; Agarwal, N.; Goel, A.; Ram, V. *J. Org. Chem.* 2003, 68, 2983].

Wherein the present invention provides a process for the preparation of novel compounds having the general formula T-2 as shown in drawing accompanying the specification represents a preferred embodiment of this process for the compounds from template T-2:

Synthesis of Template T-2

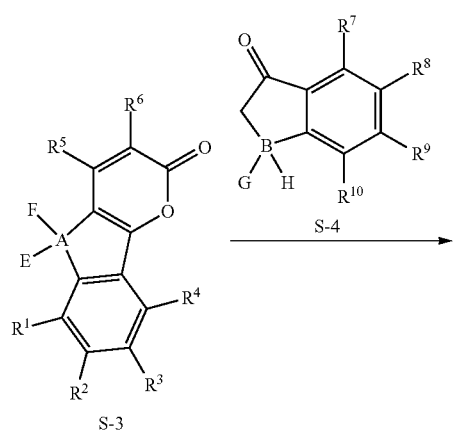

-continued e) reacting a compound having general formula S-3 with a compound having general formula S-4 to furnish a compound having the general formula T-2 wherein $R^1$, $R^2$, $R^3$, $R^4$, $R^5$, $R^6$, $R^7$, $R^8$, $R^9$, and $R^{10}$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro;

Wherein, A, B is selected from the units consisting of optionally substituted or unsubstituted one carbon unit, optionally a ketone group, optionally substituted alkene, an oxygen atom, a sulfur atom, or a nitrogen atom;

Wherein, E, F, G and/or H is selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro;

Wherein, EF or GH together may be a double bond directly linked to an oxygen atom or a methylene group or optionally substituted methylene group;

f) wherein in step e, reaction may proceeds in a common organic solvent particularly DMF, THF (but not limited to this) in the presence of a base particularly KOH, NaH, KH (but not limited to this) at a temperature ranging between −78° C. to 100° C. for a period ranging between <1 minute to 24 br, g) wherein, isolating the compound of general formula T-2 from the reaction mixture obtained in step e and purifying by chromatographic techniques;

h) The starting material of the general formula S-4 are known and the compound of the general formula S-3 has been prepared by the reaction of methyl 2-cyano/methoxycarbonyl-3,3-di(methylsulfanyl)acrylate with substituted cyclic ketone of the general formula S-4 under alkaline conditions in dry DMSO in high yields according to the procedure reported earlier [(a) Tominaga, Y.; Ushirogouchi, A.; Matsuda, Y.; Kobayashi, G. *Chem. Pharm. Bull.* 1984, 32, 3384. (b) Tominaga, Y.; Ushirogouchi, A.; Matsuda, Y. *J. Heterocycl. Chem.* 1987, 24, 1557. (c) Farhanullah; Agarwal, N.; Goel, A.; Ram, V. J. *J. Org. Chem.* 2003, 68, 2983].

Wherein the present invention provides a process for the preparation of novel compounds having the general formula T-3 as shown in drawing accompanying the specification represents a preferred embodiment of this process for the compounds from template T-3:

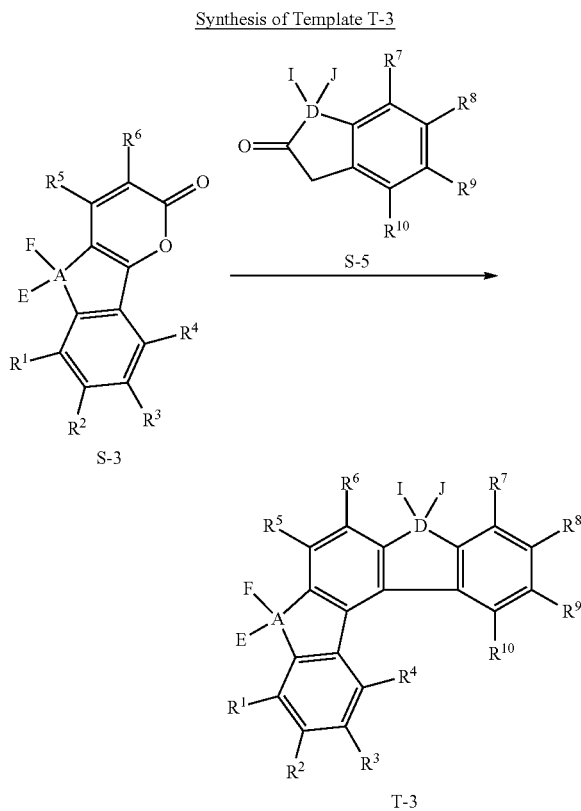

i) reacting a compound having general formula S-3 with a compound having general formula S-5 to furnish a compound having the general formula T-3 wherein $R^1$, $R^2$, $R^3$, $R^4$, $R^5$, $R^6$, $R^7$, $R^8$, $R^9$, and $R^{10}$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro;

Wherein, A, D is selected from the units consisting of optionally substituted or unsubstituted one carbon unit, optionally a ketone group, optionally substituted alkene, an oxygen atom, a sulfur atom, or a nitrogen atom;

Wherein, E, F, I and/or J is selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro;

Wherein, EF or IJ together may be a double bond directly linked to an oxygen atom or a methylene group or optionally substituted methylene group;

i) wherein in step i, reaction may proceeds in a common organic solvent particularly DMF, THF (but not limited to this) in the presence of a base particularly KOH, NaH, KH (but not limited to this) at a temperature ranging between −78° C. to 100° C. for a period ranging between <1 minute to 24 hr, j) wherein, isolating the compound of general formula T-3 from the reaction mixture obtained in step i and purifying by chromatographic techniques;

k) The starting material of the general formula S-5 are known and the compound of the general formula S-3 has been prepared by the reaction of methyl 2-cyano/methoxycarbonyl-3,3-di(methylsulfanyl)acrylate with substituted cyclic ketone of the general formula S-5 under alkaline conditions in dry DMSO in high yields according to the procedure reported earlier [(a) Tominaga, Y.; Ushirogouchi, A.; Matsuda, Y.; Kobayashi, G. *Chem. Pharm. Bull.* 1984, 32, 3384. (b) Tominaga, Y.; Ushirogouchi, A.; Matsuda, Y. *J. Heterocycl. Chem.* 1987, 24, 1557. (c) Farhanullah; Agarwal, N.; Goel, A.; Ram, V. J. *J. Org. Chem.* 2003, 68, 2983].

Photophysical Studies of the Compounds of General formula I

Figure 5:
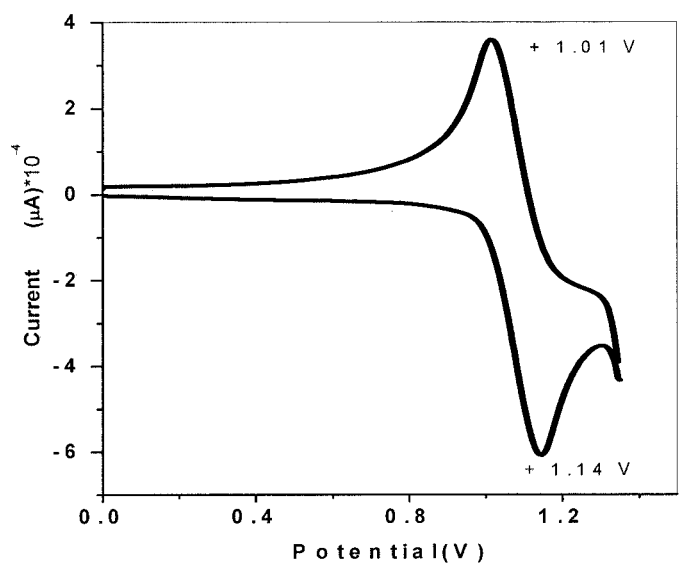
FIG. 5 illustrates cyclic voltagram of compound 14.
Figure 6:
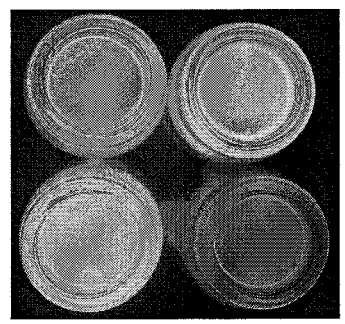
FIG. 6 illustrates green emission defect showing that donor-acceptor fluorenones can show emission in blue region which can overcome the problem of green emission defect.

The photophysical properties of all the synthesized compounds 1-5, 10-14, 45-49 and 34-38 were examined by UV-vis and fluorescence techniques (FIG. 5 and FIG. 6). Table 1 showed the $\lambda_{max}$ of their UV and fluorescence spectral data along with the extinction coefficient, and stoke's shift. These compounds produced different color emissions depending upon the nature and position of electron donor-acceptor substituents and chromophores attached on fluorene scaffolds (Table 1).

TABLE 1

Photophysical properties of fluorene (6a-e, 9a-e) and fluorenones (7a-e, 10a-e).

| Comp. | $\lambda_{max:\ abs}$ (nm)$^a$ | $\lambda_{max,\ em}$ (nm)$^b$ | Stoke's Shift (cm$^{-1}$)$^c$ | $E_{op}$ (eV)$^d$ | Emission Color$^e$ |
|---|---|---|---|---|---|
| 1 | 353 | 446 | 5900 | 3.30 | B |
| 2 | 360 | 453 | 5700 | 3.18 | B |
| 3 | 358 | 442 | 5310 | 3.19 | B |
| 4 | 362 | 462 | 5980 | 3.20 | B |
| 5 | 346 | 460 | 7170 | 3.18 | B |
| 45 | 392 | 527 | 6540 | 2.55 | YG |
| 46 | 392 | 529 | 6610 | 2.77 | YG |
| 47 | 390 | 526 | 6630 | 2.75 | YG |
| 48 | 392 | 527 | 6540 | 2.61 | YG |
| 49 | 393 | 528 | 6510 | 2.70 | YG |
| 10 | 382 | 446 | 3750 | 3.09 | B |
| 11 | 358 | 449 | 5660 | 3.20 | B |
| 12 | 358 | 451 | 5760 | 3.25 | B |
| 13 | 362 | 465 | 6120 | 3.20 | B |
| 14 | 344 | 481 | 8270 | 3.22 | B |
| 34 | 358 | — | — | — | NF |
| 35 | 348 | — | — | — | NF |
| 36 | 344 | 460 | 7330 | 3.39 | B |
| 37 | 346 | — | — | — | NF |
| 38 | 344 | 473 | 7930 | 3.38 | B |

Figure 7:
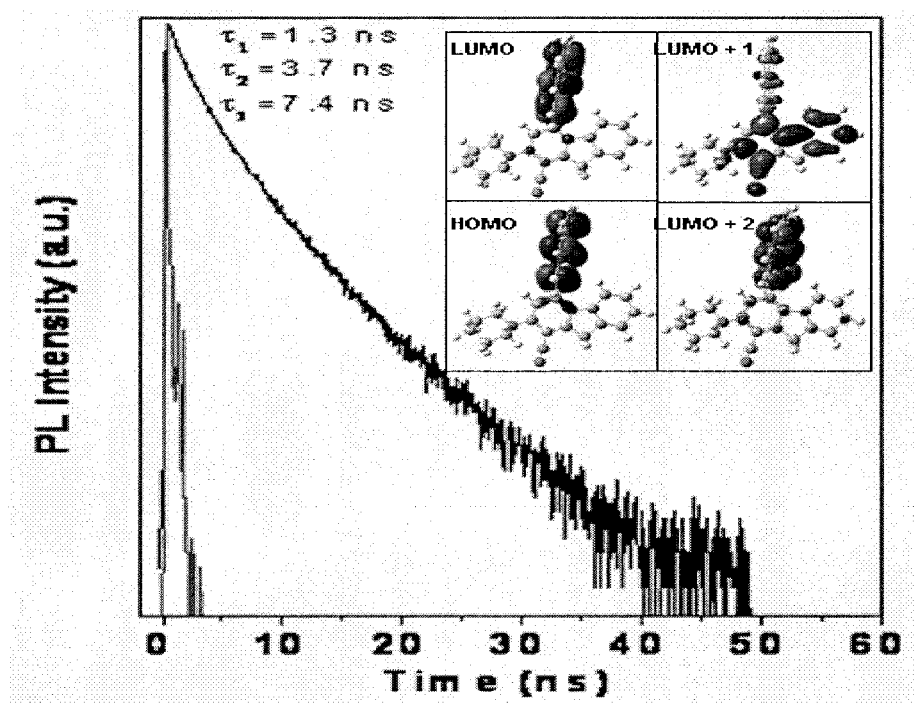
FIG. 7 illustrates the time decay experiment for the compound 14.

Cyclic voltammetric measurements were performed in Dichloromethane (DCM) using standard calomel electrode (SCE) as standard electrode and Pt as the working electrode in 0.001M tetra butyl ammonium per hexachlorate (TBAP) electrolytic conditions. FIG. 7 shows one fully reversible oxidation wave at +1.14V, corresponding to an one-electron acceptor process, indicating the ability of the molecule to undergo oxidation easily; providing scope as a good hole transporting material. The energy of the HOMO of the compound 14 compound is determined according to the equation, $[-E_{oxd} - 4.8]$ eV where $E_{oxd}$ is the potential at the onset of oxidation. The HOMO was estimated to be −5.8 eV from the oxidation onset potential. The corresponding LUMO level was calculated based on the optical band gap of 3.2 eV. The LUMO value was estimated to be −2.6 eV.

Thermal Analysis: Thermogravimetric analysis (TGA) was obtained with Perkin Elmer Diamond TGDTA analyzer. Compound 14 exhibited good thermal stability. It showed less then 100/decomposition at >300° C. under nitrogen and lost about 20% weight upto 440° C. The TGA data of selected compounds are mentioned below:

| Compd. | Temperature ($T_d$) | |
|---|---|---|
| | $T_d^a$ | $T_d^b$ |
| 5 | 183 | 212 |
| 14 | 300 | 440 |
| 49 | 359 | 516 |
| 38 | 310 | 363 |

$^a$decomposition temperature at 10% weight loss.
$^b$decomposition temperature at 20% weight loss.

Green Emission Defect

Figure 8:
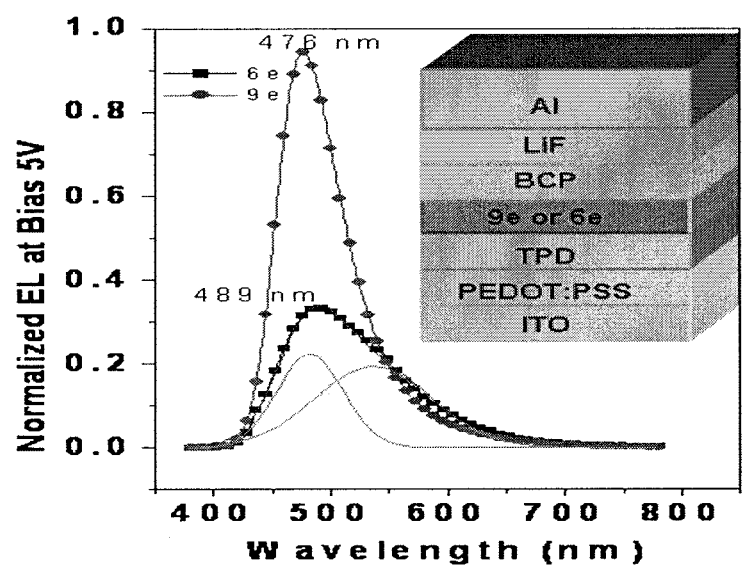
FIG. 8 EL curve of the 5 (so called 6e in device) and 14 (so called 9e in device). The inset shows the device structure; green curves show vibronic peaks of 5 at 489 nm and 540 nm FIG. 9 Shows the plot of EL wavelength as a function of voltage for the device made with and 14 compounds. Inset shows the Current-Voltage character and EL Intensity plot for both 5 and 14 compound Down inset shows pictures of OLEDs of 5 (so called 6e in device) and 14 (so called 9e in device).
Figure 10:
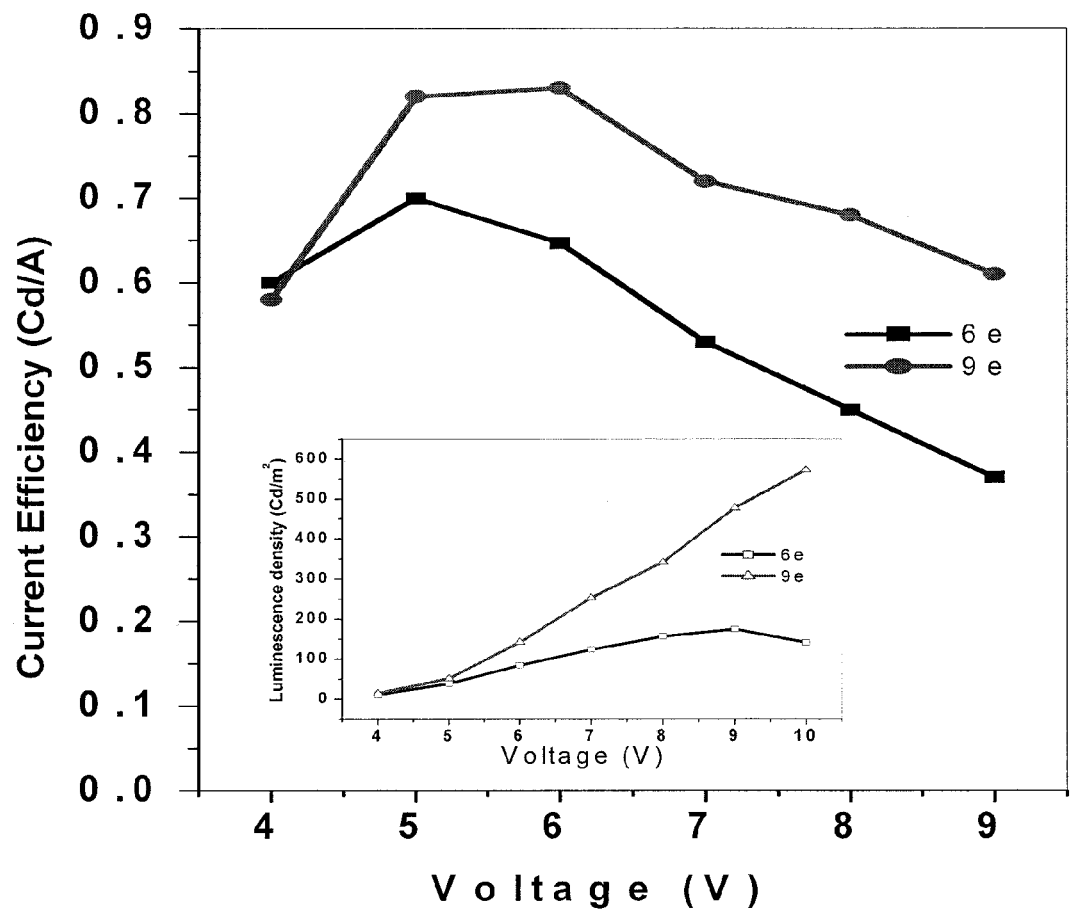
FIG. 10 Shows the Current efficiency of the device having 5 and 14 as emissive layer: The inset to the figure shows the Luminescence Density vs. Voltage Curve.

All the fluorenes (1-5) substituted at position 1 with different chromophoric groups (π-groups) showed emission in blue region (Table 1) while their corresponding fluorenones (45-49) showed emission in greenish yellow region, which revealed fluorenones to be responsible for 'green emission defect' in 2,7-fluorene-based OLEDs. When we changed the positions of these donor-acceptor and chromophoric groups like in a series of fluorenes (10-14), all fluorenes exhibited emission in the blue region and their corresponding fluorenones showed either blue fluorescence (36, 38) or no fluorescence (34, 35, 37) depending on the chromophores attached at position 4 on the fluorenone scaffold. It means that greenish yellow color emitting fluorenones (47, 49) can be converted to blue color emitting fluorenones (36, 38) by rearranging the substitution pattern on the fluorene scaffolds. In other words, preparing molecules like 4-pyrenyl-2-piperidin-1-yl-9H-fluorene-1-carbonitrile 14, where both fluorene 14 and fluorenone 38 showed emission in blue region (FIG. 8), could retain blue color purity and will overcome the problem of additional green band in fluorene-based OLED device. The OLED device shows that the $\lambda_{max}$ of PL (solution) agrees well with the EL spectra in which no additional green band was appeared (FIG. 10). This experiment suggests that green emission defect can be removed by appropriate functionalization of donor-acceptor groups on fluorene scaffold.

Figure 9:
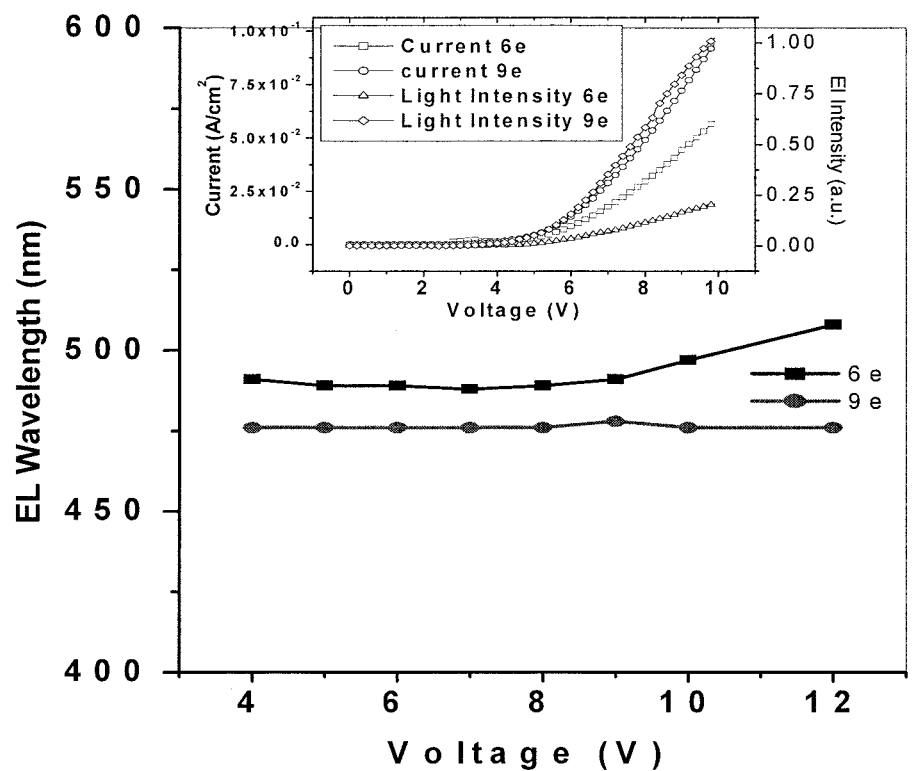
Figure 9:

Time Decay Experiments:

Further to probe the emission mechanism of this molecule, we have carried out nano-second time decay measurement. The life time decay traces of the integrated emission between 400 and 600 nm were measured in solid state as shown in FIG. 9. The time resolved PL (TRPL) decay of the compound is fitted to a tri-exponential decay model with a time constant of $\tau_1 = 1.3$, $\tau_2 = 3.7$ and $\tau_3 = 7.4$ ns. The tri-exponential decay component arises predominantly from the pyrene, fluorene and CN moieties as evident from the semi-empirical calculation as shown in FIG. 9.

Electroluminescent Device

The compounds of present invention can be used in electroluminescent devices. The basic construction of such devices comprises an anode/an organic light emitting layer/a cathode. Constructions having a hole injecting and transporting layer or an electron injecting layer suitably added to the basic construction are known. Examples of such construction include the construction of an anode/a hole injecting and transporting layer/an organic light emitting layer/a cathode and the construction of an anode/a hole injecting and transporting layer/an organic light emitting layer/an electron injecting layer/a cathode. Therefore the present invention also relates to an electronic device comprising at least one photoactive layer and or an electroactive layer positioned between two electrical contact layers, wherein at least one of the electroactive layers or the photoactive layers of the device includes the fluorene compounds of the invention. A typical device has an anode layer and a cathode layer and electroactive layers and optional layer between the anode and cathode. Adjacent to the anode is a hole injection/transport layer. Adjacent to the cathode is an optional layer comprising an electron injection/transport material. Between the hole injection/transport layer and the cathode (or optional electron transport layer) is the photoactive layer. The fluorenes of the invention can be useful in the hole injection/transport layer and/or in the photoactive layer and/or the optional electron injection/transport layer.

An electronic device of the present invention comprises of one or a plurality of layers disposed between two electrical contact layers such that at least one of the layers includes fluorenes and their pi-conjugated scaffolds having general formula I or fluorenones and their pi-conjugated scaffolds having general formula I or derivatives thereof of the present invention. The device may comprises of at least a photo active layer disposed between the said electrical contact layers, such that the photo active layer includes fluorenes and their pi-conjugated scaffolds having general formula I or fluorenones and their pi-conjugated scaffolds having general formula I or derivatives thereof of the present invention. The device may comprise at least a electro active layer disposed between two electrical contact layers, such that the electro active layer includes fluorenes and their pi-conjugated scaffolds having general formula I or fluorenone and their pi-conjugated scaffolds having general formula I or derivatives thereof of present invention. The device may comprises of at least a hole injection and or transport layer disposed between the said electrical contact layers, such that the hole injection layer and or transport layer includes fluorenes and their pi-conjugated scaffolds having general formula I or fluorenone and their pi-conjugated scaffolds having general formula I or derivatives thereof of the present invention. The device may comprises of at least an electron injection and or transport layer disposed between the said electrical contact layers, such that the electron injection and or transport layer includes fluorenes and their pi-conjugated scaffolds having general formula I or fluorenone and their pi-conjugated scaffolds having general formula I or derivatives thereof of present invention.

The present invention also relates to an electronic device comprising at least one photoactive layer positioned between two electrical contact layers, wherein at least one of the electroactive layers of the device includes the fluorene compounds of the invention. A typical device has an anode layer and a cathode layer and electroactive layers and optional layer between the anode and cathode. Adjacent to the anode is a hole injection/transport layer. Adjacent to the cathode is an optional layer comprising an electron injection/transport material. Between the hole injection/transport layer and the cathode (or optional electron transport layer) is the photoactive layer. The fluorenes of the invention can be useful in the hole injection/transport layer and/or in the photoactive layer and/or the optional electron injection/transport layer.

The device generally also includes a support (not shown) which can be adjacent to the anode or the cathode. Most frequently, the support is adjacent the anode. The support can be flexible or rigid, organic or inorganic. Generally, glass or flexible organic films are used as a support. The anode is an electrode that is particularly efficient for injecting or collecting positive charge carriers. The anode is preferably made of materials containing a metal, mixed metal, alloy, metal oxide or mixed-metal oxide. The anode may also comprise an organic material such as polyaniline as described in "Flexible light-emitting diodes made from soluble conducting polymer," Nature vol. 357, pp 477-479 (Jun. 11, 1992).

The anode layer is usually applied by a physical vapor deposition process or spin-cast process. The term "physical vapor deposition" refers to various deposition approaches carried out in vacuo. Thus, for example, physical vapor deposition includes all forms of sputtering, including ion beam sputtering, as well as all forms of vapor deposition such as e-beam evaporation and resistance evaporation. A specific form of physical vapor deposition which is useful is magnetron sputtering.

The fluorenes of the invention may function as hole transport materials in layer. Other materials which may facilitate hole injection/transport include N,N'-diphenyl-N,N'-bis(3-methylphenyl)-[1,1'-biphenyl]-4,4'-diamine (TPD) and bis[4-(N,N-diethylamino)-2-methylphenyl](4-methylphenyl)methane (MPMP), and hole transport polymers such as polyvinylcarbazole (PVK), (phenylmethyl)polysilane, poly(3,4-ethylenedioxythiophene) (PEDOT), and polyaniline (PANI); electron and hole transporting materials such as 4,4'-N,N'-dicarbazole biphenyl (BCP); or light-emitting materials with good electron and hole transport properties, such as chelated oxinoid compounds, such as tris(8-hydroxyquinolato)aluminum ($Alq_3$).

The hole injection/transport layer can be applied using any conventional means, including spin-coating, casting, and printing, such as gravure printing. The layer can also be applied by ink jet printing, thermal patterning, or physical vapor deposition.

Depending upon the application of the device, the photoactive layer can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, Electronics and Nucleonics Dictionary, 470 and 476 (McGraw-Hill, Inc. 1966).

Where the device is a light-emitting device, the photoactive layer will emit light when sufficient bias voltage is applied to the electrical contact layers. The fluorenes of the invention may be used in the light-emitting active layer. The light-emitting materials may be dispersed in a matrix of another material, with and without additives, but preferably form a layer alone. The active organic layer generally has a thickness in the range of 20-500 nm.

Where the electronic device is a photodetector, the photoactive layer responds to radiant energy and produces a signal either with or without a biased voltage. Materials that respond to radiant energy and is capable of generating a signal with a biased voltage (such as in the case of a photoconductive cells, photoresistors, photoswitches, phototransistors, phototubes) include, for example, many conjugated polymers and electroluminescent materials. Materials that respond to radiant energy and are capable of generating a signal without a biased voltage (such as in the case of a photoconductive cell or a photovoltaic cell) include materials that chemically react to light and thereby generate a signal. Such light-sensitive chemically reactive materials include for example, many conjugated polymers and electro- and photo-luminescent materials. Specific examples include, but are not limited to, MEH-PPV ("Optocoupler made from semiconducting polymers", G. Yu, K. Pakbaz, and A. J. Heeger, Journal of Electronic Materials, Vol. 23, pp 925-928 (1994); and MEH-PPV Composites with CN-PPV ("Efficient Photodiodes from Interpenetrating Polymer Networks", J. J. M. Halls et al. (Cambridge group) Nature Vol. 376, pp. 498-500, 1995).

The photoactive layer containing the active organic material can be applied from solutions by any conventional means, including spin-coating, casting, and printing. The active organic materials can be applied directly by vapor deposition processes, depending upon the nature of the materials. It is also possible to apply an active polymer precursor and then convert to the polymer, typically by heating.

The cathode is an electrode that is particularly efficient for injecting or collecting electrons or negative charge carriers. The cathode can be any metal or nonmetal having a lower work function than the first electrical contact layer (in this case, an anode).

The cathode layer is usually applied by a physical vapor deposition process. In general, the cathode layer will be patterned, as discussed above in reference to the anode layer and conductive polymer layer. Similar processing techniques can be used to pattern the cathode layer.

Optional layer can function both to facilitate electron transport, and also serve as a buffer layer or confinement layer to prevent quenching reactions at layer interfaces. Preferably, this layer promotes electron mobility and reduces quenching reactions. Examples of electron transport materials for optional layer include metal chelated oxinoid compounds, such as tris(8-hydroxyquinolato)aluminum ($Alq_3$); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ).

The device can be prepared by sequentially depositing the individual layers on a suitable substrate. Substrates such as glass and polymeric films can be used. In most cases the anode is applied to the substrate and the layers are built up from there. However, it is possible to first apply the cathode to a substrate and add the layers in the reverse order.

Device Fabrication:

Multilayer devices were fabricated to investigate the performance of a blue light-emitting material (5, 14). The following layer structure was prepared and tested: ITO/PEDOT:PSS/TPD (30 nm)/5 or 14 (60 nm)/BCP (8 nm)/LiF (0.5 nm)/Al (160 nm). While TPD was employed for hole transport purpose, BCP was chosen as the electron transport layer. PEDOT:PSS serves as an active buffer to get a sharp interface between ITO and TPD layer.

The EL characteristics of both the compounds are shown in FIG. 10. EL of compound 14 showed sharp peak at 476 nm with a FWHM of 60 rm and that of 5 compound exhibited peak at 489 nm with FWHM of 120 nm. The $\lambda_{max}$ of PL (solution) of 14 agrees well with the EL spectrum, while a red shift of 29 nm is observed in EL of 5. The additional green emission band at 540 nm in 5 appears to be, coming from the oxidation of fluorene 5 to fluorenone 7e during device operation, which resulted in the broadening of the EL peak of device 5. Such an additional green EL band is distinctly absent in 14 (FIG. 10). To further evaluate the electrochemical stability of fluorenes 5 and 14, the EL spectra of these fluorenes were recorded with increase in applied voltage at an interval of IV. The shift in wavelength of 5 and 14 is plotted in FIG. 11. A remarkable red shift is observed in the device of 5 with an increase in the applied voltage, while the device 14 was found to be stable even under bias stress. This shows the effectiveness of the model 14 in containing the wavelength to blue region. The oxidation of 5 leads to emergence of fluorenone responsible for green emission defect and a bathochromic shift.

Figures 1, 11:
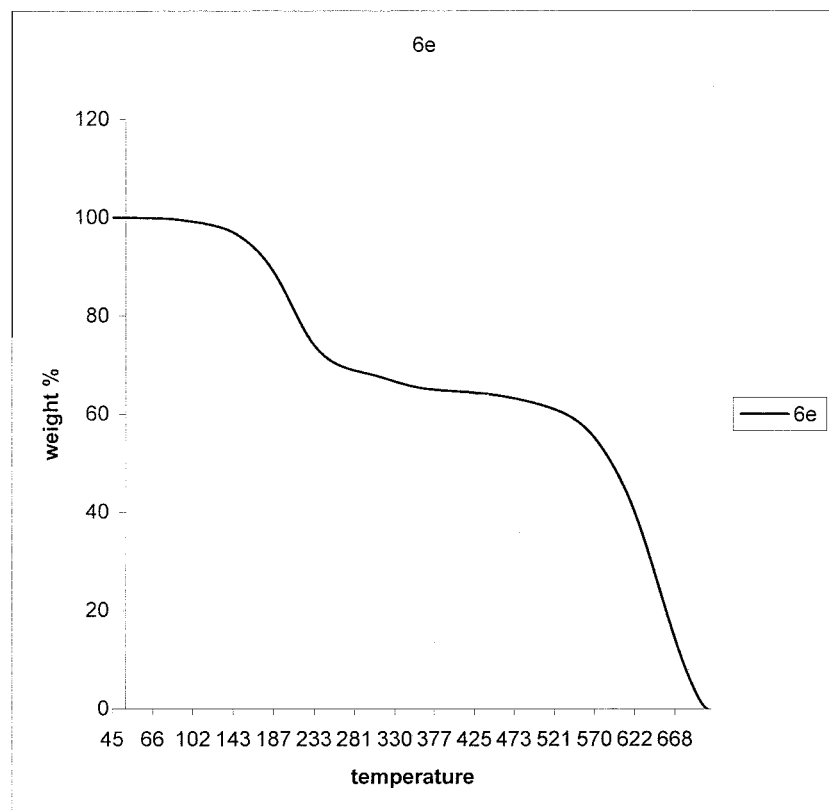
FIG. 11 illustrates Thermogravimetric analysis of selected compounds.
Figures 2, 11:
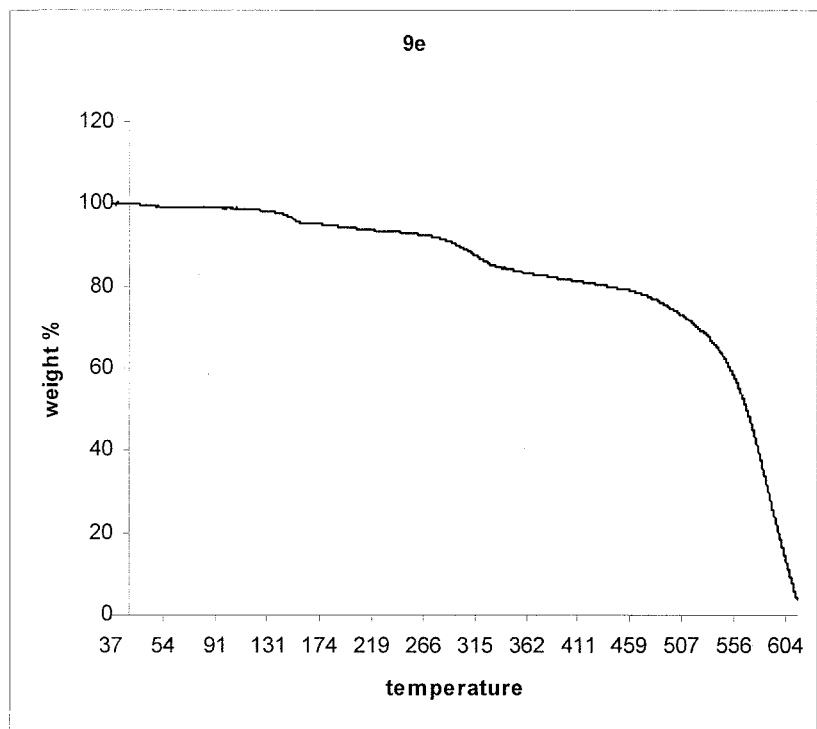
Figures 3, 11:
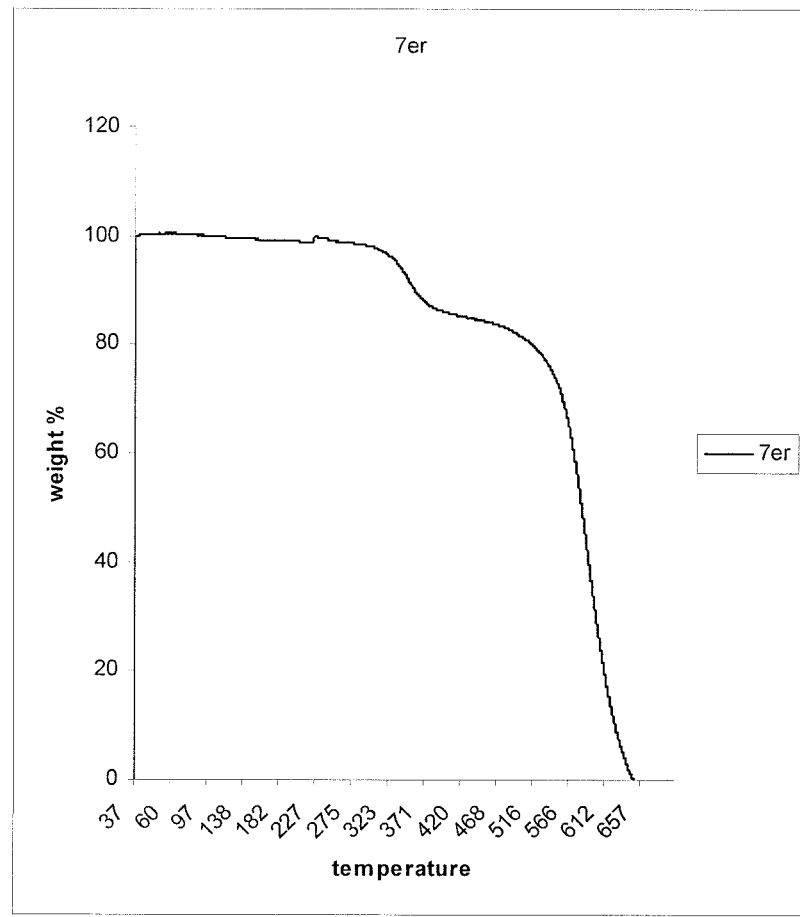
Figures 4, 11:
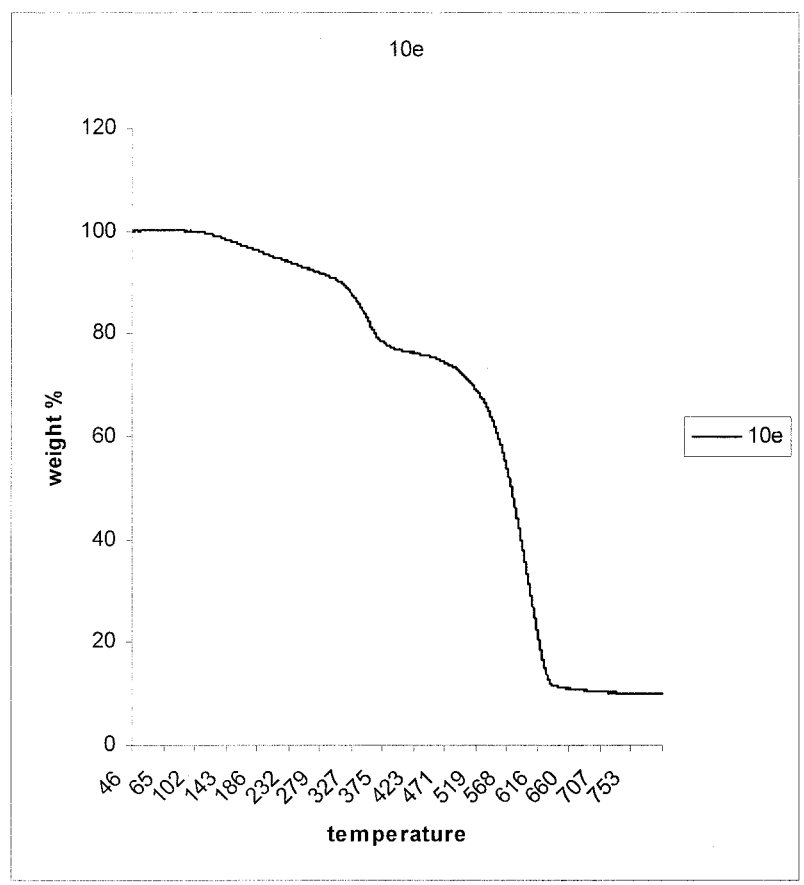

The current density-voltage and luminance-voltage characteristics of device 5 and 14 are plotted in inset of FIG. 11. The current efficiency of both the molecules is shown in FIG. 11. The device made, of 14 is more efficient than the 5 device under similar processing conditions and device structure. Despite an overall device thickness of about –100 nm, the device for the 14 compound shows substantially low (3.5V) 'ON' voltage with good luminescence efficiency (0.85 Cd/A) and good brightness as shown in the inset of FIG. 11. At a luminescence density of 572.5 Cd/m/z the efficiency is still 0.61 Cd/A, a 27% decrease from the maximum efficiency (FIG. 12). In case of 5 device, the efficiency decreases from 0.7 Cd/A to 0.37 Cd/A, a decrease of 47%.

The (x,y) co-ordinates of emission color produced by 5 and 14 are (0.23, 0.37) and (0.16, 0.26) respectively in the chromaticity graphs. The 14 gives more saturated and bright colour in comparison to 5 and also remain comparatively stable during the device operation as evident from FIGS. 11 and 12. The purity of the color clearly confirms the role of appropriately swapped donor-acceptor moieties in the fluorene ring.

A feature of the present invention is to use a novel approach for overcoming the problem of additional green emission band in fluorene-based light emitting diodes by incorporating electron donor, acceptor and/or chromophoric groups on fluorene scaffolds at appropriate positions.

Another feature of the invention is to use a novel approach for overcoming the problem of additional green emission band in fluorene-based light emitting diodes by functionalizing fluorenones with electron donor and acceptor groups in a way so that they show emission in blue region through hypsochromic shift of green emission band caused by usual fluorenone compounds.

Following examples are given by way of illustration and should not construed the scope of the present invention.

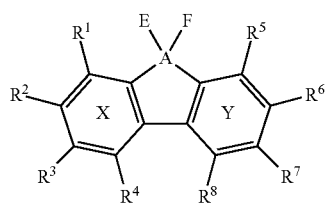

T-1

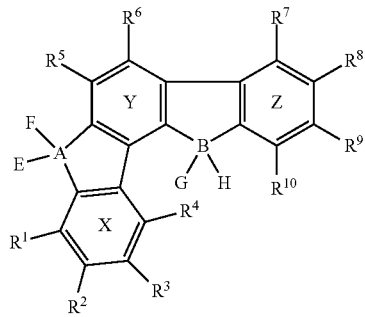

T-2

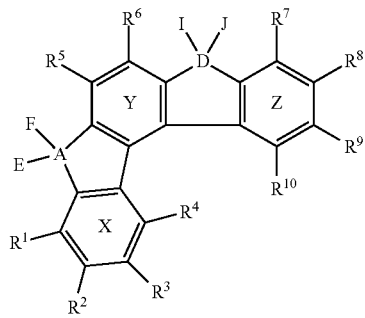

T-3

General Procedure for the Synthesis of Compounds 1-23:

A mixture of 6-aryl-2-oxo-4-amino-2H-pyran-3-carbonitriles (1 mmol), substituted/unsubstituted indanone-1 or substituted/unsubstituted indanone-2 (1 mmol) and sodium hydride (1-2 mmol) in THF (5-mL) was stirred at room temperature for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent.

General Procedure for the Synthesis of 24-33:

A mixture of the respective 2-oxo-4-amino-2,5-dihydro-indeno[1,2-b]pyran-3-carbonitrile/2-oxo-4-amino-5,6-dihydro-2H-benzo[h]chromene-3-carbonitrile (1 mmol), the corresponding substituted/unsubstituted indanone-1 or substituted/unsubstituted indanone-2 (1 mmol) and sodium hydride (1-2 mmol) in THF (5 mL) was stirred under nitrogen at room temperature for <5 min. The reaction mixture was poured into ice water with vigorous stirring and then neutralized with dilute aqueous HCl. The solid thus obtained was filtered and purified on a silica gel column using ethylacetate-hexane as a eluent.

General Procedure for the Oxidation of Fluorenes to Fluorenones (34-51):

A solution of fluorenes (1 mmol) in an organic solvent (preferably THF) was added sodium hydride (1-2 mmol) and was stirred at room temperature for less than five minutes. After completion, the reaction solvent was evaporated under vacuum and the crude solid obtained was quenched with ice water and subsequently neutralized by dilute HCl. The yellow precipitate thus obtained was filtered and purified on a silica gel column using ethyl acetate-hexane as eluent.

1) 1-Phenyl-3-pyrrolidin-1-yl-9H-fluorene-4-carbonitrile

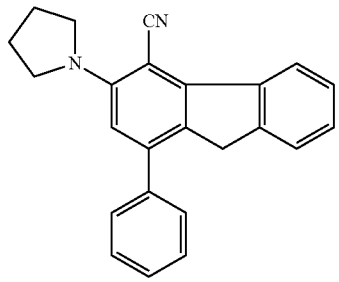 [SMILES: N#Cc1c(N2CCCC2)cc(-c2ccccc2)c2c1-c1ccccc1C2]

A mixture of 2-oxo-6-phenyl-4-(pyrrolidin-1-yl)-2H-pyran-3-carbonitrile (266 mg), indanone-1 (132 mg) and NaH (31 mg) in THIF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 158-160° C.; ESIMS 336 (M$^+$); IR (KBr) 2203 cm$^{-1}$ (CN); $^1$H NMR (200 MHz, CDCl$_3$) δ 2.01-2.05 (m, 4H, 2CH$_2$), 3.68-3.72 (m, 4H, 2CH$_2$), 3.78 (s, 2H, CH$_2$), 6.63 (s, 1H, ArH), 7.30-7.51 (m, 8H, ArH), 8.63 (d, J=7.8 Hz, 1H, ArH); HRMS calcd. for C$_{24}$H$_{20}$N$_2$ 336.1627. Found 336.1599.

2) 1-Phenyl-3-piperidin-1-yl-9H-fluorene-4-carbonitrile

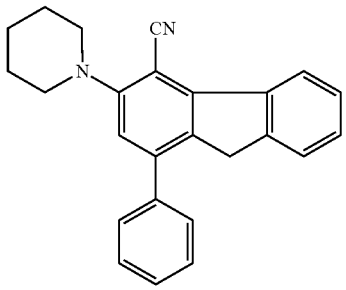 [SMILES: N#Cc1c(N2CCCCC2)cc(-c2ccccc2)c2c1-c1ccccc1C2]

A mixture of 2-oxo-6-phenyl-4-(piperidin-1-yl)-2H-pyran-3-carbonitrile (280 mg), indanone-1 (132 mg) and NaH (36 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 156-156° C.; ESIMS 351 (M$^+$+1); IR (KBr) 2214 cm$^{-1}$ (CN);

3) 1-Naphthalen-1-yl-3-piperidin-1-yl-9H-fluorene-4-carbonitrile

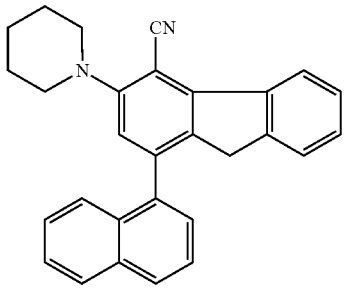 [SMILES: N#Cc1c(N2CCCCC2)cc(-c2cccc3ccccc23)c2c1-c1ccccc1C2]

A mixture of 6-(naphthalen-1-yl)-2-oxo-4-(piperidin-1-yl)-2H-pyran-3-carbonitrile (330 mg), indanone-1 (132 mg) and NaH (39 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 188-190° C.; ESIMS 401 (M$^+$+1); IR (KBr) 2214 cm$^{-1}$ (CN); $^{13}$C NMR (75.53 MHz, CDCl$_3$): δ 22.86, 25.03, 34.33, 52.76, 97.13, 116.68, 117.50, 121.36, 123.53, 124.14, 124.34, 124.87, 124.91, 125.22, 125.94, 127.00, 127.19, 127.25, 129.68, 132.40, 135.37, 136.53, 138.21, 141.05, 143.26, 143.37, 156.43.

4) 1-Naphthalen-2-yl-3-piperidin-1-yl-9H-fluorene-4-carbonitrile

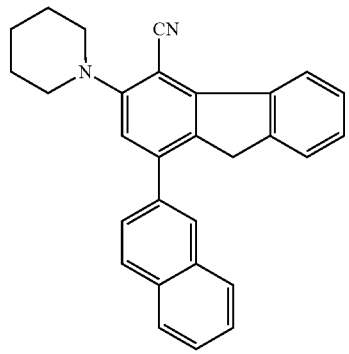 [SMILES: N#Cc1c(N2CCCCC2)cc(-c2ccc3ccccc3c2)c2c1-c1ccccc1C2]

A mixture of 6-(naphthalen-2-yl)-2-oxo-4-(piperidin-1-yl)-2H-pyran-3-carbonitrile (330 mg), indanone-1 (132 mg) and NaH (39 mg) in THF was stirred for <5 min. After completion, the reaction solvent was evaporated under vacuum to dryness and crude, solid was quenched with ice water and subsequently neutralized with dil. HCl, finally purified by column chromatography using ethylacetate-hexane as eluent. White solid; mp 136-138° C.; ESIMS 401 (M$^+$+1); IR (KBr) 2214 cm$^{-1}$ (CN); HRMS calcd. for C$_2$H$_{24}$N$_2$ 400.1940 Found 400.1939.

5) 3-Piperidin-1-yl-1-pyren-1-yl-9H-fluorene-4-carbonitrile

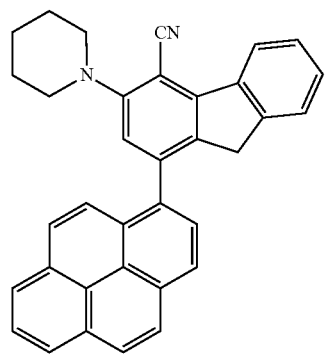 [SMILES: N#Cc1c(N2CCCCC2)cc(-c2ccc3ccc4cccc5ccc2c3c45)c2c1-c1ccccc1C2]

A mixture of 2-oxo-4-(piperidin-1-yl)-6-(pyren-1-yl)-2H-pyran-3-carbonitrile (404 mg), indanone-1 (132 mg) and NaH (43 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 114-116° C.; ESIMS 475 (M$^+$+1); IR (KBr) 2215 cm$^-$ (CN); $^1$H NMR (300 Hz, CDCl$_3$) δ 1.60-1.69 (m, 2H, CH$_2$), 1.84-1.93 (m, 4H, 2CH$_2$), 3.25-3.31 (m, 4H, 2CH$_2$), 3.56 (s, 2H, CH$_2$), 7.12 (s, 1H, ArH), 7.35-7.38 (m, 2H, ArH), 7.45-7.54 (m, 1H, ArH), 7.77-7.83 (m, 1H, ArH), 7.96-8.10 (m, 3H, ArH), 8.16-8.23 (m, 3H, ArH), 8.28 (t, J=7.5 Hz, 2H, ArH), 8.67 (d, J=7.8 Hz, 1H, ArH).

6) 3,5-Dimethyl-furan-2-yl)-3-piperidin-1-yl-9H-fluorene-4-carbonitrile

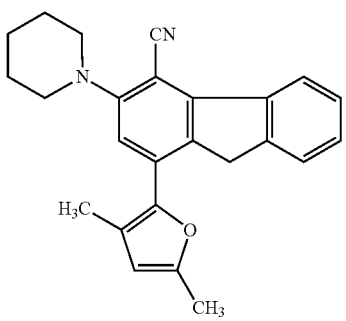 [SMILES: Cc1cc(C)c(-c2cc(N3CCCCC3)c(C#N)c3c2Cc2ccccc2-3)o1]

A mixture of 6-(3,5-dimethylfuran-2-yl)-2-oxo-4-(piperidin-1-yl)-2H-pyran-3-carbonitrile (298 mg), indanone-1 (132 mg) and NaH (36 mg) in THF was stirred for <5 min. After completion, the reaction solvent was evaporated under vacuum to dryness and crude: solid was quenched with ice water and subsequently neutralized with dil. HCl, finally purified by column chromatography-using ethylacetate-hexane as eluent. White solid; mp 140-141° C.; ESMS 369 (M$^+$+1); IR (KBr) 2216 cm$^{-1}$ (CN).

7) 1-(4-Fluoro-phenyl)-3-piperidin-1-yl-9H-fluorene-4-carbonitrile

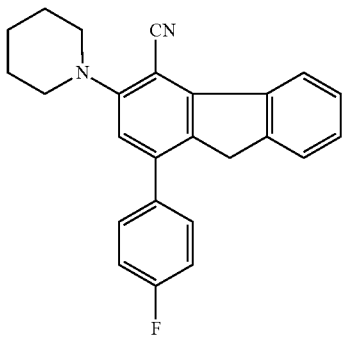 [SMILES: N#Cc1c(N2CCCCC2)cc(-c2ccc(F)cc2)c2c1-c1ccccc1C2]

A mixture of 6-(4-fluorophenyl)-2-oxo-4-(piperidin-1-yl)-2H-pyran-3-carbonitrile (298 mg), indanone-1 (132 mg) and NaH (36 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. Yellow solid; mp 176-178° C.; FAB MS 368 (M$^+$); IR (KBr) 2220 cm$^{-1}$ (CN); HRMS calcd. for C$_{25}$H$_{21}$FN$_2$ 368.16888. Found 368.16806.

8) 3-Piperidin-1-yl-1-thiophen-2-yl-9H-fluorene-4-carbonitrile

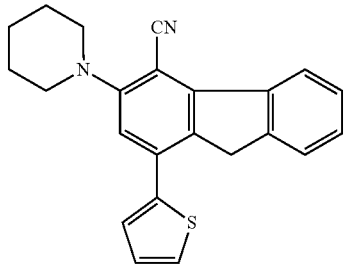 [SMILES: N#Cc1c(N2CCCCC2)cc(-c2cccs2)c2c1-c1ccccc1C2]

A mixture of 2-oxo-4-(piperidin-1-yl)-6-(thiophen-2-yl)-2H-pyran-3-carbonitrile (286 mg), indanone-1 (132 mg) and NaH (37 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent Yellowish solid; mp 152-154° C.; ESMS 357 (M$^+$+1); IR (KBr). 2217 cm$^{-1}$ (CN); HRMS calcd. for C$_{23}$H$_{20}$N$_2$S 356.1347 found 356.1139.

9) 4-Furan-2-yl-2-piperidin-1-yl-9H-fluorene-1-carbonitrile

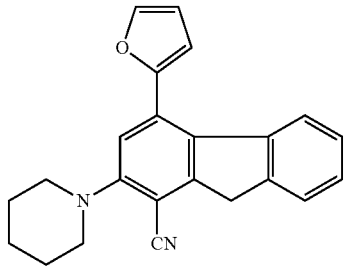 [SMILES: N#Cc1c(N2CCCCC2)cc(-c2ccco2)c2c1Cc1ccccc1-2]

A mixture of 6-(furan-2-yl)-2-oxo-4-(piperidin-1-yl)-2H-pyran-3-carbonitrile (270 mg), indanone-2 (132 mg) and NaH (28 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent White solid; mp 160-162° C.; ESMS 341 (M$^+$+1); IR (KBr) 2218 cm$^{-1}$ (CN).

10) 4-Phenyl-2-pyrrolidin-1-yl-9H-fluorene-1-carbonitrile

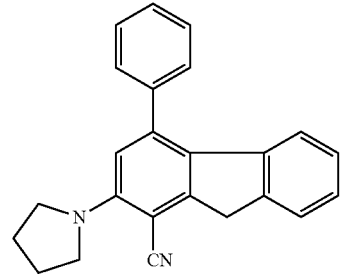 [SMILES: N#Cc1c(N2CCCC2)cc(-c2ccccc2)c2c1Cc1ccccc1-2]

A mixture of 2-oxo-6-phenyl-4-(pyrrolidin-1-yl)-2H-pyran-3-carbonitrile (266 mg), indanone-2 (132 mg) and NaH (38 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 210-212° C.; MS (FAB) 336 (M+); IR (KBr) 2208 cm$^{-1}$ (CN); $^{13}$C NMR (75.53 MHz, CDCl$_3$): δ 24.50, 36.66, 48.88, 90.0, 113.64, 118.40, 119.85, 123.28, 123.92, 125.16, 126.79, 126.90, 127.27, 127.31, 139.10, 139.87, 140.33, 141.29, 147.16, 150.32; HRMS calcd. for C$_{24}$H$_{20}$N$_2$ 336.16265 Found 336.16232.

11) 4-Phenyl-2-piperidin-1-yl-9H-fluorene-1-carbonitrile

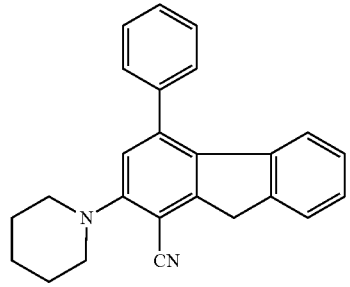 [SMILES: N#Cc1c(N2CCCCC2)cc(-c2ccccc2)c2c1Cc1ccccc1-2]

A mixture of 2-oxo-6-phenyl-4-(piperidin-1-yl)-2H-pyran-3-carbonitrile (280 mg), indanone-2 (132 mg) and NaH (44 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 140-141° C.; ESIMS 351 (M$^+$+1); IR (KBr) 2219 cm$^{-1}$ (CN); $^{13}$C NMR (75.53 MHz, CDCl$_3$): δ 22.89, 24.96, 36.00, 52.15, 100.45, 116.08, 117.93, 120.78, 123.54, 125.06, 125.34, 126.97, 127.35, 127.42, 131.32, 138.85, 139.20, 140.94, 141.01, 149.06, 153.62.

12) 4-Naphthalen-1-yl-2-piperidin-1-yl-9H-fluorene-1-carbonitrile

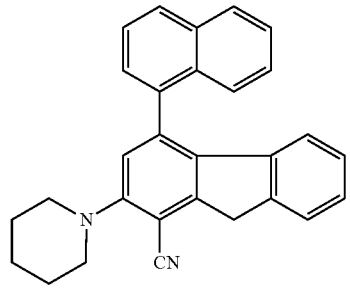 [SMILES: N#Cc1c(N2CCCCC2)cc(-c2cccc3ccccc23)c2c1Cc1ccccc1-2]

A mixture of 6-(naphthalen-1-yl)-2-oxo-4-(piperidin-1-yl)-2H-pyran-3-carbonitrile (330 mg), indanone-2 (132 mg) and NaH (41 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 148-149° C.; ESIMS 401 (M$^+$1); IR (KBr) 2213 cm$^{-1}$ (CN); $^{13}$C NMR (75.53 MHz, CDCl$_3$): δ 22.84, 24.94, 36.08, 52.16, 100.72, 116.12, 118.56, 120.75, 123.36, 124.30, 124.48, 124.92, 125.0, 125.36, 125.43, 127.09, 127.29, 130.15, 132.29, 132.64, 136.40, 138.86, 138.99, 140.82, 148.79, 153.65.

13) 4-Naphthalen-2-yl-2-piperidin-1-yl-9H-fluorene-1-carbonitrile

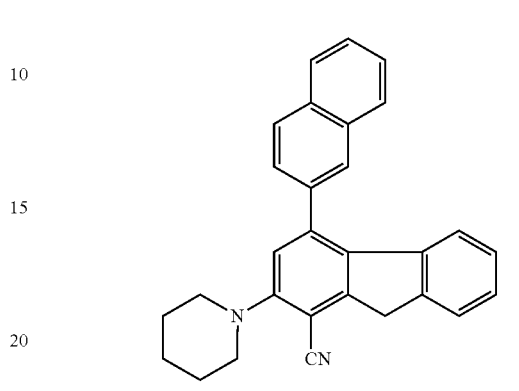

A mixture of 6-(naphthalen-2-yl)-2-oxo-4-(piperidin-1-yl)-2H-pyran-3-carbonitrile (330 mg), indanone-2 (132 mg) and NaH (43 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 142-144° C.; ESIMS 401 (M$^+$+1); IR (KBr) 2215 cm$^{-1}$ (CN).

14) 2-Piperidin-1-yl-4-pyren-1-yl-9H-fluorene-1-carbonitrile

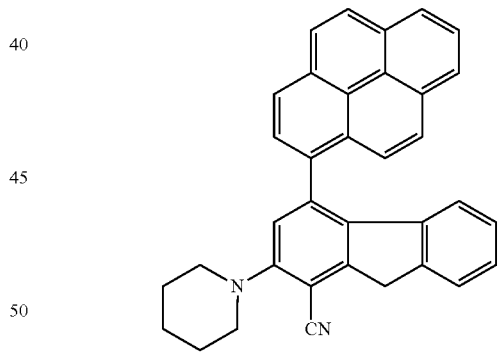

A mixture of 2-oxo-4-piperidin-1-yl)-6-(pyren-1-yl)-2H-pyran-3-carbonitrile, (404 mg), indanone-2 (132 mg) and NaH (45 mg) in THF was stirred for <5 min. After completion, the reaction solvent was evaporated under vacuum to dryness and crude solid was quenched with ice water and subsequently neutralized with dil. HCL, finally purified by column chromatography using ethylacetate-hexane as eluent. White solid; mp 168-169° C.; ESIMS 475 (M$^+$+1), IR (KBr) 2217 cm$^{-1}$ (CN); $^1$H NMR (300 MHz, CDCl$_3$) δ 1.60-1.68 (m, 2H, CH$_2$), 1.79-1.89 (m, 4H, 2CH$_2$), 3.28-3.34 (m, 4H, 2CH$_2$), 4.21 (s, 2H, CH$_2$), 5.98 (d, J=7.8 Hz, 1H, ArH), 6.68 (t, J=7.5 Hz, 1H, ArH), 7.02 (s, 1H, ArH), 7.08 (t, J=7.5 Hz, 1H, ArH), 7.51 (d, J=7.5 Hz, 1H, ArH), 7.79 (d, J=9.2 Hz, 1H, ArH), 7.94 (s, 1H, Ar), 7.96-8.10 (m, 2H, ArH), 8.16-8.22 (m, 3H, ArH), 8.28 (d, J=7.5 Hz, 1H, ArH), 8.33 (d, J=7.8 Hz, 1H, ArH); HRMS calcd. for $C_{35}H_{26}N_2$ 474.2096. Found 474.2093.

15) 4-(4-Methoxy-phenyl)-2-piperidin-1-yl-9H-fluorene-1-carbonitrile

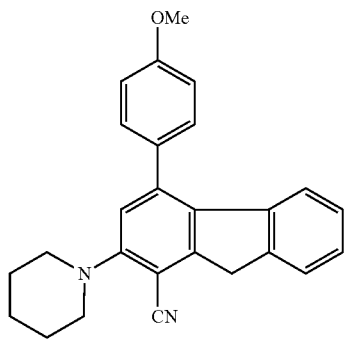 [SMILES: COc1ccc(-c2cc(N3CCCCC3)c(C#N)c3c2-c2ccccc2C3)cc1]

A mixture of 6-(4-methoxyphenyl)-2-oxo-4-(piperidin-1-yl)-2H-pyran-3-carbonitrile (310 mg), indanone-2 (132 mg) and NaH (40 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 202-204° C.; MS 380 (M⁺); IR (KBr) 2210 cm⁻¹ (CN).

16) 2-Piperidin-1-yl-4-p-tolyl-9H-fluorene-1-carbonitrile

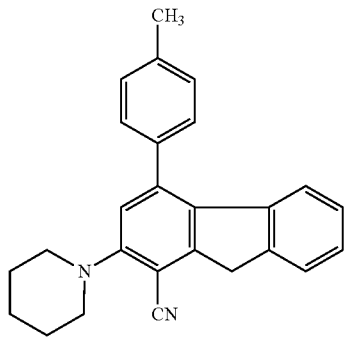 [SMILES: Cc1ccc(-c2cc(N3CCCCC3)c(C#N)c3c2-c2ccccc2C3)cc1]

A mixture of 2-oxo-4-(piperidin-1-yl)-6-p-tolyl-2H-pyran-3-carbonitrile (294 mg), indanone-2, (132 mg) and NaH (29 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 162-164° C.; ESMS 365 (M⁺+1); IR (KBr) 2213 cm⁻¹ (CN); HRMS calcd. for $C_{26}H_{24}N_2$ 364.1940 found 364.1936.

17) 4-(4-Chloro-phenyl)-2-pyrrolidin-1-yl-9H-fluorene-carbonitrile

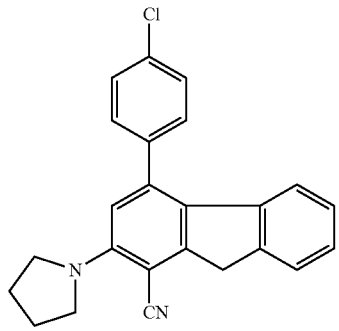 [SMILES: N#Cc1c(N2CCCC2)cc(-c2ccc(Cl)cc2)c2c1Cc1ccccc1-2]

A mixture of 6-(4-chlorophenyl)-2-oxo-4-(pyrrolidin-1-yl)-2H-pyran-3-carbonitrile (300 mg), indanone-2 (132 mg) and NaH (33 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 197-199° C.; FAB MS 370 (M⁺); IR (KBr) 2217 cm⁻¹ (CN).

18) 2-Pyrrolidin-1-yl-4-p-tolyl-9H-fluorene-1-carbonitrile

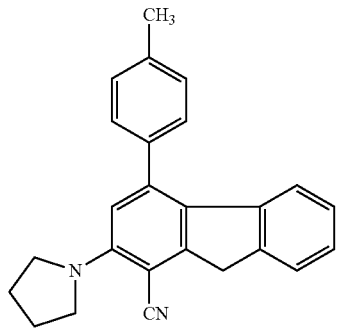 [SMILES: Cc1ccc(-c2cc(N3CCCC3)c(C#N)c3c2-c2ccccc2C3)cc1]

A mixture of 2-oxo-4-(pyrrolidin-1-yl)-6-p-tolyl-2H-pyran-3-carbonitrile (280 mg), indanone-2 (132 mg) and NaH (39 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 182-184° C.; ESMS 351 (M⁺+1); IR (KBr) 2205 cm⁻¹ (CN); ¹H NMR (200 MHz, CDCl₃) δ 1.99-2.06 (m, 4H, 2CH₂), 2.48 (s, 3H, CH₃), 3.63-3.72 (m, 4H, 2CH₂) δ 4.03 (s, 2H, CH₂), 6.45 (s, 1H, ArH), 6.80 (d, J=7.6 Hz, 1H, ArH), 7.03-7.18 (m, 2H, ArH), 7.27-7.36 (m, 4H, ArH), 7.47 (d, J=7.0 Hz, 1H, ArH).

19) 2-Piperidin-1-yl-4-thiophen-2-yl-9H-fluorene-1-carbonitrile

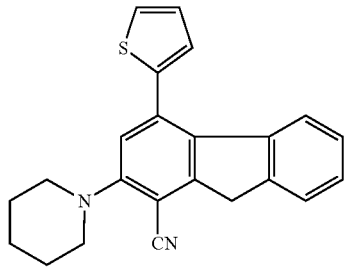

A mixture of 2-oxo-4-(piperidin-1-yl)-6-(thiophen-2-yl)-2H-pyran-3-carbonitrile (286 mg), indanone-2 (132 mg) and NaH (41 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 148-150° C.; FAB MS 357 ($M^+$+1); IR (KBr) 2215 $cm^{-1}$ (CN), $^1H$ NMR (200 MHz, $CDCl_3$) δ 1.60-1.64 (m, 2H, $CH_2$), 1.79-1.82 (m, 4H, $2CH_2$), 3.20-3.25 (m, 4H, $2CH_2$), 4.10 (s, 2H, $CH_2$), 6.92 (s, 1H, ArH), 7.10-7.24 (m, 5H, ArH & CH), 7.49-7.54 (m, 2H, ArH & CH); HRMS calcd. for $C_{23}H_{20}N_2S$ 356.13472. Found 356,13580.

20) 2-Piperidin-1-yl-4-(4-pyrrol-1-yl-phenyl)-9H-fluorene-1-carbonitrile

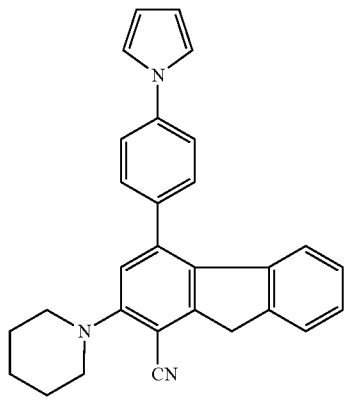 [SMILES: N#Cc1c(N2CCCCC2)cc(-c2ccc(-n3cccc3)cc2)c2c1Cc1ccccc1-2]

A mixture of 6-(4-(1H-pyrrol-1-yl)phenyl)-2-oxo-4-(piperidin-1-yl)-2H-pyran-3-carbonitrile (345 mg), indanone-2 (132 mg) and NaH (47 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 224-226° C.; ESMS 416 ($M^+$+ 1); IR (KBr) 2211 $cm^{-1}$ (CN); $^1H$ NMR (200 MHz, $CDCl_3$) δ 1.60-1.66 (m, 2H, $CH_2$), 1.79-1.82 (m, 4H, $2CH_2$), 3.22-3.30 (m, 4H, $2CH_2$) δ 6.42 (t, J=2 Hz, 2H, CH), 6.82 (s, 1H, ArH), 6.93 (d, J=7.8 Hz, 1H, ArH), 7.07 (t, J=7.5 Hz, 1H, ArH), 7.17-7.24 (m; 4H, ArH & CH), 7.46-7.59 (m, 4H, ArH).

21) 4-(4-Acetyl-phenyl)-2-piperidin-1-yl-9H-fluorene-1-carbonitrile

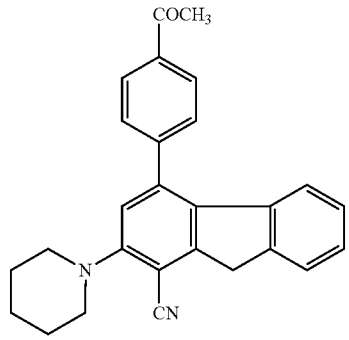 [SMILES: CC(=O)c1ccc(-c2cc(N3CCCCC3)c(C#N)c3c2-c2ccccc2C3)cc1]

A mixture of 6-(4-acetylphenyl)-2-oxo-4-(piperidin-1-yl)-2H-pyran-3-carbonitrile (322 mg), indanone-2 (132 mg) and NaH (43 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; yield 76%; mp 182-184° C.; ESMS 393 ($M^+$+1); IR (KBr) 2213 $cm^{-1}$ (CN); $^1H$ NMR (200 MHz, $CDCl_3$) δ 1.60-1.65 (m, 2H, $CH_2$), 1.79-1.83 (m, 4H, $2CH_2$), 2.71 (s, 3H, $CH_3$), 3.22-3.26 (m, 4H, $2CH_2$), 4.10 (s, 2H, $CH_2$), 6.78-6.83 (m, 2H, ArH), 7.05 (m, 1H, ArH), 7.18-7.26 (m, 1H, ArH), 7.50-7.60 (m, 3H, ArH), 8.11 (d, J=8.0 Hz, 2H, ArH).

22) 4-(4-Fluoro-phenyl)-2-piperidin-1-yl-9H-fluorene-1-carbonitrile

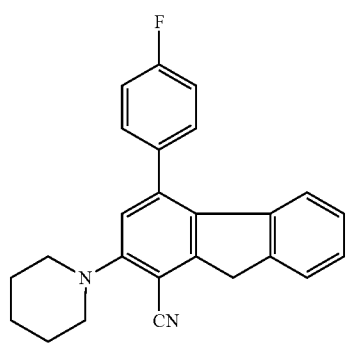 [SMILES: N#Cc1c(N2CCCCC2)cc(-c2ccc(F)cc2)c2c1Cc1ccccc1-2]

A mixture of 6-(4-fluorophenyl)-2-oxo-4-(piperidin-1-yl)-2H-pyran-3-carbonitrile (298 mg), indanone-2 (132 mg) and NaH (41 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; yield 81%; mp 130-132° C.; ESMS 369 ($M^+$+1); IR (KBr) 2216 $cm^{-1}$ (CN).

23) 4-(4-Bromo-phenyl)-2-piperidin-1-yl-9H-fluorene-1-carbonitrile

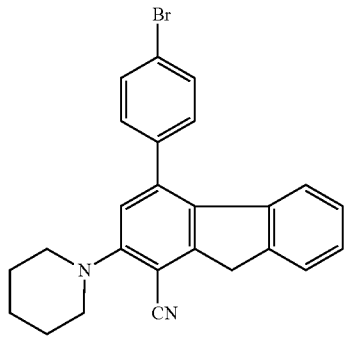 [SMILES: N#Cc1c(N2CCCCC2)cc(-c2ccc(Br)cc2)c2c1Cc1ccccc1-2]

A mixture of 6-(4-bromophenyl)-2-oxo-4-(piperidin-1-yl)-2H-pyran-3-carbonitrile (358 mg), indanone-2 (132 mg) and NaH (31 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 212-212° C.; ESIMS 430 (M$^+$+2); IR (KBr) 2211 cm$^{-1}$ (CN).

24) 6-Piperidin-1-yl-7,12-dihydro-indeno[1,2-a]fluorene-5-carbonitrile

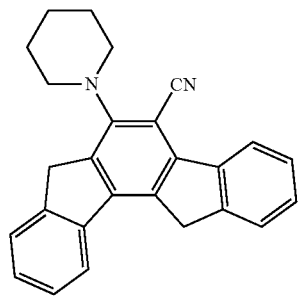 [SMILES: N#Cc1c2c(c3c(c1N1CCCCC1)Cc1ccccc1-3)Cc1ccccc1-2]

A mixture of 2-oxo-4-(piperidin-1-yl)-2,5-dihydroindeno[1,2-b]pyran-3-carbonitrile (292 mg), indanone-1 (132 mg) and NaH (41 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 186-188° C.; $^1$H NMR (200 MHz, CDCl$_3$) δ 1.66-1.70 (m, 2H, CH$_2$), 1.81-1.85 (m, 2H, CH$_2$), 3.34-3.42 (m, 4H, CH$_2$), 4.11 (s, 2H, CH$_2$), 4.17 (s, 2H, CH$_2$), 7.40-7.46 (m, 4H, ArH), 7.60-7.68 (m, 2H, ArH), 7.92 (d, 1H, J=7.8 Hz, ArH), 8.52 (d, 1H, J=7.5 Hz, ArH); MS (ESI) 363 (M+1).

25) 6-Pyrrolidin-1-yl-7,12-dihydro-indeno[1,2-a]fluorene-5-carbonitrile

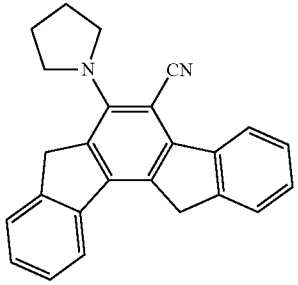 [SMILES: N#Cc1c2c(c3c(c1N1CCCC1)Cc1ccccc1-3)Cc1ccccc1-2]

A mixture of 2-oxo-4-(pyrrolidin-1-yl)-2,5-dihydroindeno[1,2-b]pyran-3-carbonitrile (278 mg), indanone-1 (132 mg) and NaH (46 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 158-160° C.; $^1$H NMR (300 MHz, CDC$_3$) δ 2.01-2.10 (m, 2H, CH$_2$), 3.75-3.85 (m, 4H, 2CH$_2$), 4.12-4.15 (m, 4H, 2CH$_2$), 7.38-7.50 (m, 4H, ArH), 7.58-7.67 (m, 2H, ArH), 7.95 (d, J=7.3 Hz, 1H, ArH), 8.62 (d, J=7.5 Hz, 1H, ArH); IR (KBr) 2199 cm$^{-1}$ (CN); MS (ESI) 349 (M$^+$+1).

26) 3-Methoxy-6-piperidin-1-yl-7,12-dihydro-indeno[1,2-a]fluorene-5-carbonitrile

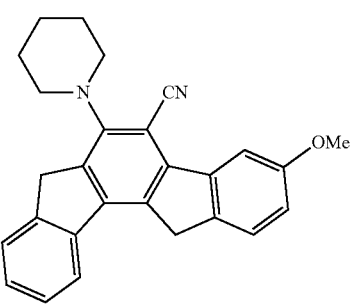 [SMILES: COc1ccc2c(c1)-c1c(C#N)c(N3CCCCC3)c3c(c1C2)-c1ccccc1C3]

A mixture of 2-oxo-4-(piperidin-1-yl)-2,5-dihydroindeno[1,2-b]pyran-3-carbonitrile (292 mg), 6-methoxyindanone-1 (162 mg) and NaH (48 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 216-218° C.; IR (KBr) 2213 cm$^{-1}$ (CN); MS (ESI) 392 (M$^+$); $^{13}$C NMR (150 MHz, CDCl$_3$) δ 24.39, 26.94, 35.47, 36.96, 53.14, 55.54, 99.39, 110.62, 113.05, 118.84, 122.72, 123.26, 124.94, 127.11, 127.93, 131.65, 132.25, 134.54, 140.38, 142.59, 144.41, 144.74, 146.32, 152.27, 160.02.

27) 7-Piperidin-1-yl-5,8-dihydro-indeno[2,1-c]fluorene-6-carbonitrile

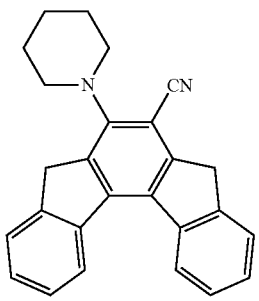 [SMILES: N#Cc1c2c(c3c(c1N1CCCCC1)Cc1ccccc1-3)-c1ccccc1C2]

A mixture of 2-oxo-4-(piperidin-1-yl)-2,5-dihydroindeno[1,2-b]pyran-3-carbonitrile (292 mg), indanone-2 (132 mg) and NaH. (40 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 200-202° C.; IR (KBr) 2215 cm$^{-1}$ (CN); MS (ESI) 363 (M$^+$+1) HRMS Calculated for $C_{26}H_{22}N_2$ 362.1783 measured 362.1792.

28) 7-Pyrrolidin-1-yl-5,8-dihydro-indeno[2,1-c]fluorene-6-carbonitrile

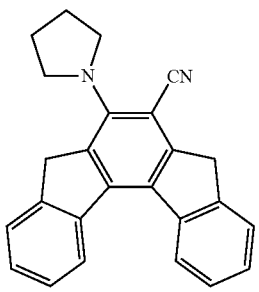 [SMILES: N#Cc1c2c(c3c(c1N1CCCC1)Cc1ccccc1-3)-c1ccccc1C2]

A mixture of 2-oxo-4-(pyrrolidin-1-yl)-2,5-dihydroindeno[1,2-b]pyran-3-carbonitrile (278 mg), indanone-2 (132 mg) and NaH (42 mg) in THF was stirred for <5 min. After completion, the reaction solvent was evaporated under vacuum to dryness and crude solid was quenched with ice water aid subsequently neutralized with dil. HCl, finally purified by column chromatography using ethylacetate-hexane as eluent. White solid; mp 206-208° C.; $^1$H NMR (300 MHz, CDCl$_3$) δ 2.03-2.11 (m, 4H, 2CH$_2$), 3.85-3.92 (m, 4H, 2CH$_2$), 4.07 (s, 2H, CH$_2$), 4.11 (s, 2H, CH$_2$), 729-7.35 (m, 1H, ArH), 7.38-7.52 (m, 3H, ArH), 7.58-7.62 (m, 2H, ArH), 8.34 (d, J=7.8 Hz; 1H, ArH), 8.55 (d, J=7.68 Hz, 1H, ArH); IR (KBr) 2213 cm$^{-1}$ (CN); MS (ESI) 349 (M$^+$+1).

29) 7-(4-Methyl-piperidin-1-yl)-5,8-dihydro-indeno[2,1-c]fluorene-6-carbonitrile

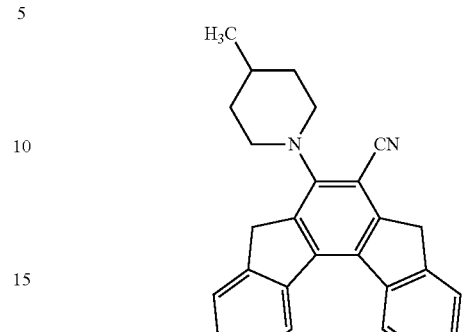

A mixture of 4-(4-methylpiperidin-1-yl)-2-oxo-2,5-dihydroindeno[1,2-b]pyran-3-carbonitrile (306 mg), indanone-2 (132 mg) and NaH (45 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 166-168° C.; IR (KBr) 2215 cm$^{-1}$ (CN); MS (ESI) 377 (M$^+$+1).

30) 11-Methoxy-7-piperidin-1-yl-5,8-dihydro-indeno[2,1-c]fluorene-6-carbonitrile

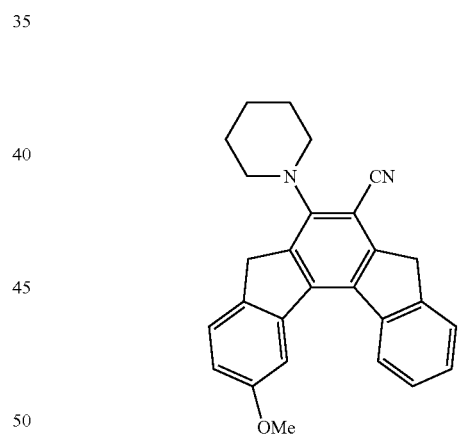

A mixture of 8-methoxy-2-oxo-4-(piperidin-1-yl)-2,5-dihydroindeno[1,2-b]pyran-3-carbonitrile (322 mg), indanone-2 (132 mg) and NaH (39 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid mp 180-182° C.; IR (KBr) 2212 cm$^{-1}$ (CN); MS (ESI) 393 (M$^+$+1); $^{13}$C NMR (150 MHz, CDCl$_3$) δ 26.22, 35.46, 38.54, 51.70, 94.61, 119.87, 122.42, 122.68, 124.68, 124.79, 127.09, 127.17, 127.64, 127.77, 129.66, 132.09, 139.48, 140.39, 142.58, 144.25, 144.40, 144.54, 149.42.

31) 7-Piperidin-1-yl-5,9-dihydro-6H-indeno[2,1-c]phenanthrene-8-carbonitrile

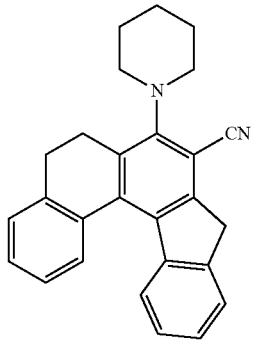 [SMILES: N#Cc1c2c(c3c(c1N1CCCCC1)CCc1ccccc1-3)-c1ccccc1C2]

A mixture of 2-oxo-4-(piperidin-1-yl)-5,6-dihydro-2H-benzo[h]chromene-3-carbonitrile (306 mg), indanone-2 (132 mg) and NaH (29 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 170-172° C.; IR (KBr) 2218 cm$^{-1}$ (CN); MS (ESI) 377 (M$^+$+1); $^1$H NMR (200 MHz, CDCl$_3$) δ 1.61-1.65 (m, 6H, 3CH$_2$), 2.77-2.81 (m, 4H, 2CH$_2$), 3.22-3.25 (m, 4H, 2CH$_2$), 4.06 (s, 2H, 2CH$_2$), 7.13-7.37 (m, 5H, ArH), 7.56 (d, J=7.21 Hz, 1H, ArH), 7.86-7.94 (m, 2H, ArH).

32) 7-Pyrrolidin-1-yl-5,9-dihydro-6H-indeno[2,1-c]phenanthrene-8-carbonitrile

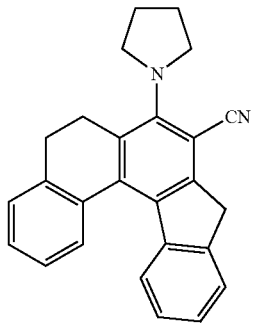 [SMILES: N#Cc1c2c(c3c(c1N1CCCC1)CCc1ccccc1-3)-c1ccccc1C2]

A mixture of 2-oxo-4-(pyrrolidin-1-yl)-5,6-dihydro-2H-benzo[h]chromene-3-carbonitrile (292 mg), indanone-2 (132 mg) and NaH (28 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 220-222° C.; IR (KBr) 2204 cm$^{-1}$ (CN); MS (ESI) 364 (M$^+$+2).

33) 7-(4-Methyl-piperidin-1-yl)-5,9-dihydro-6H-indeno[2,1-c]phenanthrene-8-carbonitrile

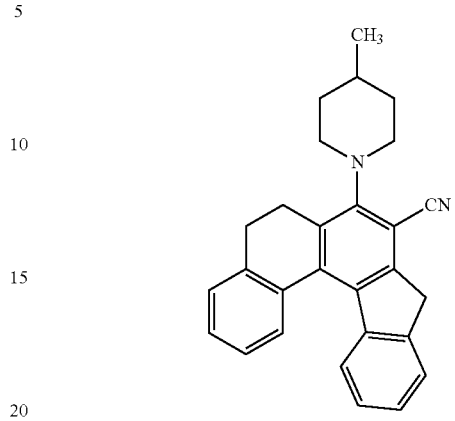

A mixture of 4-(4-methylpiperidin-1-yl)-2-oxo-5,6-dihydro-2H-benzo[h]chromene-3-carbonitrile (320 mg), indanone-2 (132 mg) and NaH (36 mg) in THF was stirred for <5 min. After completion, the reaction solvent was evaporated under vacuum to dryness and crude solid was quenched with ice water and subsequently neutralized with dil. HCl, finally purified by column chromatography using ethylacetate-hexane as eluent. White solid; mp 152-154° C.; IR (KBr) 2212 cm$^{-1}$ (CN); MS (ESI) 391 (M+11).

34) 9-Oxo-4-phenyl-2-pyrrolidin-1-yl-9H-fluorene-1-carbonitrile

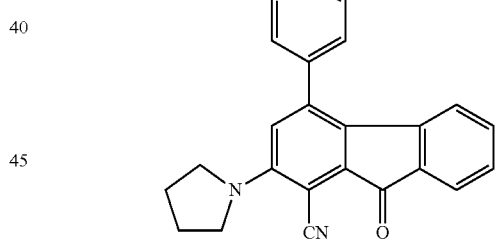

A solution of 4-phenyl-2-(pyrrolidin-1-yl)-9H-fluorene-1-carbonitrile (336 mg) in THF was added sodium hydride (25 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Light red solid; mp 166-168° C.; ESIMS 351 (M$^+$+1); IR (KBr) 2215 (CN), 1717 cm$^{-1}$ (CO); $^1$H NMR (300 Hz, CDCl$_3$) δ 1.97-2.10 (m, 4H, CH$_2$), 3.67-3.73 (m, 4H, 2CH$_2$), 6.43-6.48 (m, 1H, ArH), 6.59 (s, 1H, ArH), 7.04-7.12 (m, 2H, ArH), 7.40-7.47 (m, 2H, ArH), 7.48-7.54 (m, 3H, ArH), 7.55-7.59 (m, 1H, ArH); $^{13}$C NMR (75.53 MHz, CDCl$_3$): δ 24.50, 49.37, 88.60, 115.58, 11927, 120.14, 123.11, 126.0, 127.12, 127.33, 127.49, 129.34, 132.13, 133.40, 136.26, 137.69, 141.23, 142.34, 149.32, 189.94.

35) 9-Oxo-4-phenyl-2-piperidin-1-yl-9H-fluorene-1-carbonitrile

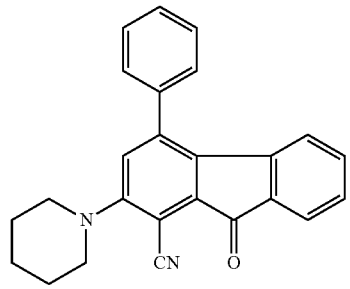 [SMILES: N#Cc1c(N2CCCCC2)cc(-c2ccccc2)c2c1C(=O)c1ccccc1-2]

A solution of 4-phenyl-2(piperidin-1-yl)-9H-fluorene-1-carbonitrile (350 mg) in THF was added sodium hydride (27 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Light red solid; mp 220-222° C.; ESIMS 365 ($M^+$+1); IR (KBr) 2220 (CN), 1709 $cm^{-1}$ CO).

36) 4-Naphthalen-1-yl-9-oxo-2-piperidin-1-yl-9H-fluorene-1-carbonitrile

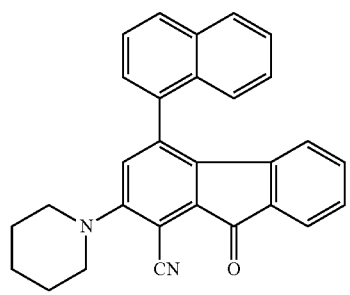 [SMILES: N#Cc1c(N2CCCCC2)cc(-c2cccc3ccccc23)c2c1C(=O)c1ccccc1-2]

A solution of 4-(naphthalen-1-yl)-2-(piperidin-1-yl)-9H-fluorene-1-carbonitrile (400 mg) in THF was added sodium hydride (37 mg) and was stirred at 0-5° C. for less than five minutes. After completion, the reaction solvent was evaporated under vacuum and the crude solid obtained was quenched with ice water and subsequently neutralized by dilute HCL. The precipitate thus obtained was filtered and purified on a silica gel column using ethyl acetate-hexane as eluent. Light red solid; mp 202-204° C.; ESIMS 0.415 ($M^+$+1); IR (KBr) 2221 (CN), 1719 $cm^{-1}$ (CO), HRMS calcd. for $C_{29}H_{22}N_2O$ 414.1732. Found 414.1714.

37) 4-Naphthalen-2-yl-9-oxo-2-piperidin-1-yl-9H-fluorene-1-carbonitrile

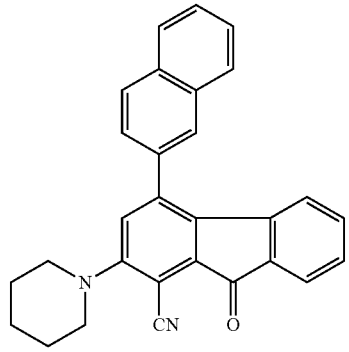 [SMILES: N#Cc1c(N2CCCCC2)cc(-c2ccc3ccccc3c2)c2c1C(=O)c1ccccc1-2]

A solution of 4-(naphthalen-2-yl)-2-(piperidin-1-yl)-9H-fluorene-1-carbonitrile (400 mg) in THF was added sodium hydride (32 mg) and was stirred at 0-5° C. for less than five minutes. After completion, the reaction solvent was evaporated under vacuum and the crude solid obtained was quenched with ice water and subsequently neutralized by dilute HCL. The precipitate thus obtained was filtered and purified on a silica gel column using ethyl acetate-hexane as eluent. Light red solid; mp 182-184° C.; ESIMS 415 ($M^+$+1); IR (KBr) 2213 (CN), 1695 $cm^{-1}$ (CO).

38) 9-Oxo-2-piperidin-1-yl-4-pyren-1-yl-9H-fluorene-1-carbonitrile

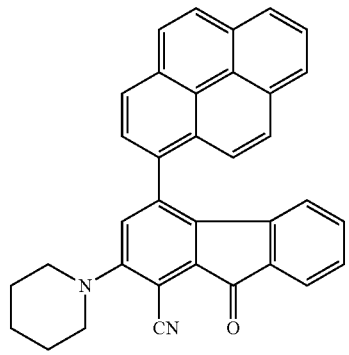 [SMILES: N#Cc1c(N2CCCCC2)cc(-c2ccc3ccc4cccc5ccc2c3c45)c2c1C(=O)c1ccccc1-2]

A solution of 2-(piperidin-1-yl)-4-(pyren-1-yl)-9H-fluorene-1-carbonitrile (474 mg) in THF was added sodium hydride (42 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Light red solid; mp 180-182° C.; ESMS 489 (M+1); IR (KBr) 2217 (CN), 1713 $cm^{-1}$ (CO).

39) 9-Oxo-2-piperidin-1-yl-4-thiophen-2-yl-9H-fluorene-1-carbonitrile

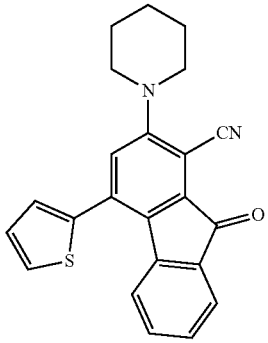 [SMILES: N#Cc1c(N2CCCCC2)cc(-c2cccs2)c2c1C(=O)c1ccccc1-2]

A solution of 2-(piperidin-1-yl)-4-(thiophen-2-yl)-9H-fluorene-1-carbonitrile (356 mg) in THF was added sodium hydride (29 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Red solid; yield 73%; mp 226-228° C.; ESMS 371 (M$^+$+1); IR (KBr) 1710 cm$^{-1}$ (CO), 2220 (CN).

40) 4-Furan-2-yl-2-piperidin-1-yl-9H-fluorene-1-carbonitrile

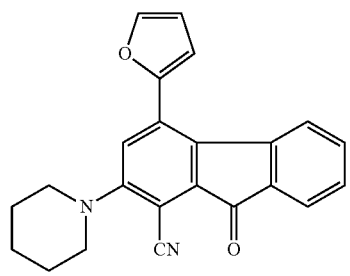 [SMILES: N#Cc1c(N2CCCCC2)cc(-c2ccco2)c2c1C(=O)c1ccccc1-2]

A solution of 4-(furan-2-yl)-2-(piperidin-1-yl)-9H-fluorene-1-carbonitrile (340 mg) in THF was added sodium hydride (31 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Red solid; mp 182-184° C.; ESMS 355 (M$^+$+1); IR (KBr) 1713 cm$^{-1}$ (CO), 2218 (CN).

41) 4-(4-Methoxy-phenyl)-9-oxo-2-piperidin-1-yl-9H-fluorene-1-carbonitrile

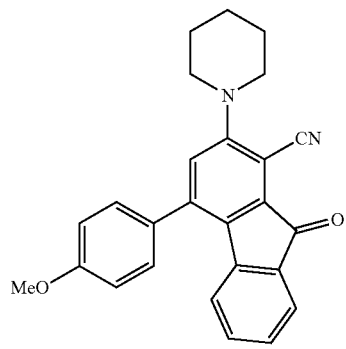 [SMILES: COc1ccc(-c2cc(N3CCCCC3)c(C#N)c3c2-c2ccccc2C3=O)cc1]

A solution of 4-(4-methoxyphenyl)-2-(piperidin-1-yl)-9H-fluorene-1-carbonitrile (380 mg) in THF was added sodium hydride (33 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Red solid; mp 210-212° C.;. FAB MS 395 (M$^+$); IR (KBr) 2210 (CN), 1703 cm$^{-1}$ (CO); HRMS calcd. for $C_{26}H_{22}N_2O_2$ 394.1681 found 394, 1689.

42) 4-(4-Fluoro-phenyl)-9-oxo-2-piperidin-1-yl-9H-fluorene-1-carbonitrile

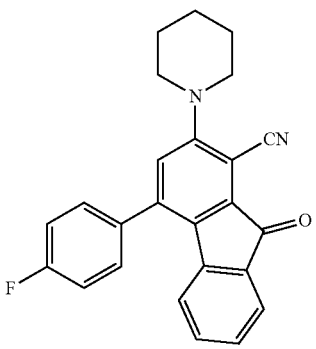 [SMILES: N#Cc1c(N2CCCCC2)cc(-c2ccc(F)cc2)c2c1C(=O)c1ccccc1-2]

A solution of 4-(4-fluorophenyl)-2-(piperidin-1-yl)-9H-fluorene-1-carbonitrile (368 mg) in THF was added sodium hydride (38 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Red solid; mp 152-154° C.; ESMS 383 (M$^+$+1); IR (KBr) 1708 cm$^{-1}$ (CO), 2221 (CN); HRMS calcd. for $C_{25}H_{19}FN_2O$ 382.1481 found 382.1471.

43) 9-Oxo-2-piperidin-1-yl-4-p-tolyl-9H-fluorene-1-carbonitrile

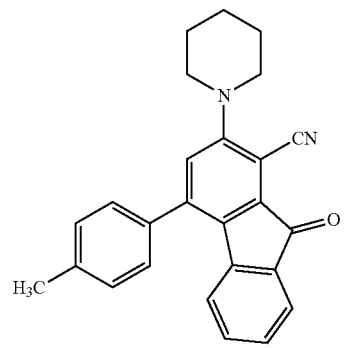 [SMILES: Cc1ccc(-c2cc(N3CCCCC3)c(C#N)c3c2-c2ccccc2C3=O)cc1]

A solution of 2-(piperidin-1-yl)-4-p-tolyl-9H-fluorene-1-carbonitrile (364 mg) in THF was added sodium hydride (40 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Red solid; mp 230-232° C.; ESMS 379 (M$^+$+1); IR (KBr) 1703 cm$^{-1}$ (CO), 2219 (CN); $^1$H NMR (300 MHz, CDCl$_3$) δ 1.60-1.64 (m, 2H, CH$_2$), 1.79-1.84 (m, 4H, 2CH$_2$), 2.48 (s, 3H, CH$_3$), 3.19-3.24 (m, 4H, 2CH$_2$), 6.65-6.70 (m, 1H, ArH), 6.87 (s, 1H, ArH), 7.14-7.19 (m, 2H, ArH), 7.28-7.33 (m, 4H, ArH), 7.63-7.67 (m, 1H, ArH). HRMS calcd. for C$_{26}$H$_{22}$N$_2$O 378.1732 found 378.1728.

44) 9-Oxo-2-pyrrolidin-1-yl-4-p-tolyl-9H-fluorene-1-carbonitrile

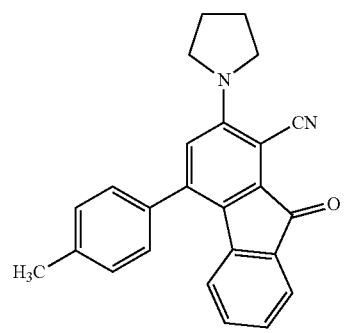 [SMILES: Cc1ccc(-c2cc(N3CCCC3)c(C#N)c3c2-c2ccccc2C3=O)cc1]

A solution of 2-(pyrrolidin-1-yl)-4-p-tolyl-9H-fluorene-1-carbonitrile (350 mg) in THF was added sodium hydride (42 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Red solid; yield 76%; mp 162-164° C.; ESMS 365 (M$^+$+1); IR (KBr) 1716 cm$^{-1}$ (CO) 2214 (CN).

45) 9-Oxo-1-phenyl-3-pyrrolidin-1-yl-9H-fluorene-4-carbonitrile

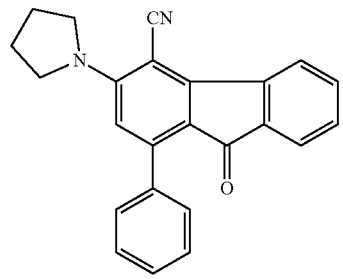 [SMILES: N#Cc1c(N2CCCC2)cc(-c2ccccc2)c2c1-c1ccccc1C2=O]

A solution of 1-phenyl-3-(pyrrolidin-1-yl)-9H-fluorene-4-carbonitrile (336 mg) in THF was added sodium hydride (45' mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Yellow solid; mp 202-204° C.; ESMS 351 (M$^+$+1); IR (KBr) 2206 (CN), 1695 cm$^{-1}$ (CO); $^1$H NMR (300 Hz, CDCl$_3$) δ 2.05-2.07 (m, 4H, 2CH$_2$), 3.77-3.81 (m, 4H, 2CH$_2$), 6.35 (s, 1H, ArH), 7.31-7.60 (m, 8H, ArH), 8.39 (d, J=7.6 Hz, 1H, ArH).

46) 9-Oxo-1-phenyl-3-piperidin-1-yl-9H-fluorene-4-carbonitrile

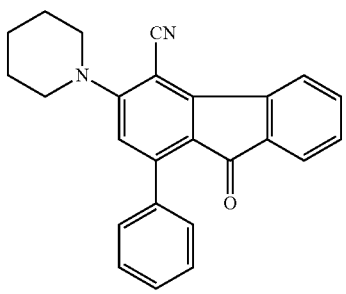 [SMILES: N#Cc1c(N2CCCCC2)cc(-c2ccccc2)c2c1-c1ccccc1C2=O]

A solution of 1-phenyl-3-(piperidin-1-yl)-9H-fluorene-4-carbonitrile (350 mg) in THF was added sodium hydride (34 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Yellow solid; mp 166-168° (C; ESIMS 365 (M$^+$+1); IR (KBr) 2219 (CN), 1705 cm$^{-1}$ (CO); $^{13}$C NMR (75.53 MHz, CDCl$_3$): δ 22.68, 24.67, 51.55, 95.24, 115.94, 118.11, 120.97, 121.16, 122.41, 126.70, 127.64, 129.33, 133.10, 133.94, 135.61, 139.20, 145.60, 149.61, 158.96, 188.36.

47) 1-Naphthalen-1-yl-9-oxo-3-piperidin-1-yl-9H-fluorene-4-carbonitrile

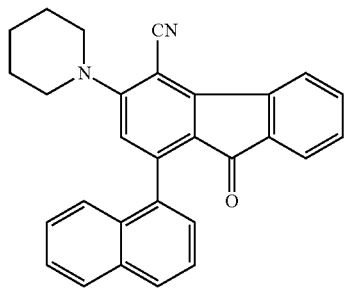 [SMILES: N#Cc1c(N2CCCCC2)cc(-c2cccc3ccccc23)c2c1-c1ccccc1C2=O]

A solution of 1-(naphthalen-1-yl)-3-(piperidin-1-yl)-9H-fluorene-4-carbonitrile (400 mg) in THF was added sodium hydride (39 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Yellow solid; mp 180-182° C.; ESIMS 415 (M-+1); IR (KBr) 2213 (CN), 1707 cm$^{-1}$ (CO); $^{13}$C NMR (75.53 MHz, CDCl$_3$): δ 22.65, 24.68, 51.57, 95.45, 115.96, 118.89, 121.27, 122.49, 122.80, 123.78, 123.92, 124.68, 124.78, 125.04, 127.22, 127.57, 129.35, 130.02, 132.05, 133.10, 133.93, 134.13, 139.41, 143.51, 149.06, 158.86, 187.99.

48) 1-Naphthalen-2-yl-9-oxo-3-piperidin-1-yl-9H-fluorene-4-carbonitrile

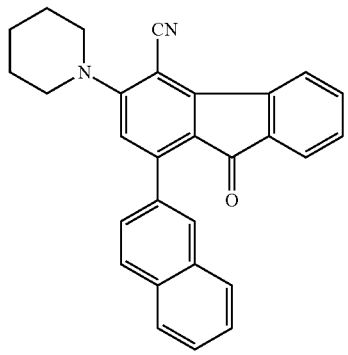 [SMILES: N#Cc1c(N2CCCCC2)cc(-c2ccc3ccccc3c2)c2c1-c1ccccc1C2=O]

A solution of 1-(naphthalen-2-yl)-3-(piperidin-1-yl)-9H-fluorene-4-carbonitrile (400 mg) in THF was added sodium hydride (39 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Yellow solid; mp 166-167° C.; ESIMS 415 (M$^+$+1); IR (KBr) 2218 (CN), 1712 cm$^{-1}$ (CO); HRMS calcd. for C$_9$H$_{22}$N$_2$O 414.1732. Found 414.1735.

49) 9-Oxo-3-piperidin-1-yl-1-pyren-1-yl-9H-fluorene-4-carbonitrile

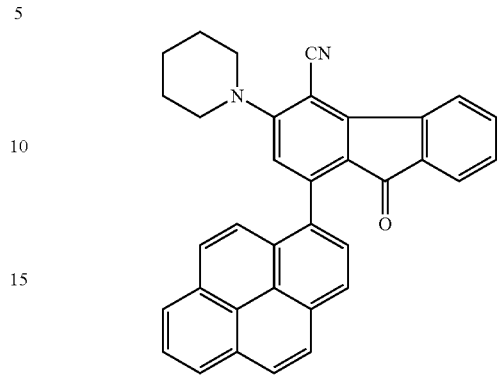

A solution of 3-(piperidin-1-yl)-1-(pyren-1-yl)$_9$H-fluorene-4-carbonitrile (474 mg) in THF was added sodium hydride (48 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Yellow solid; mp 220-222° C.; MS (FAB) 488 (M$^+$); IR (KBr) 2218 (CN), 1708 cm$^{-1}$ (CO).

50) 9-Oxo-3-piperidin-1-yl-1-thiophen-2-yl-9H-fluorene-4-carbonitrile

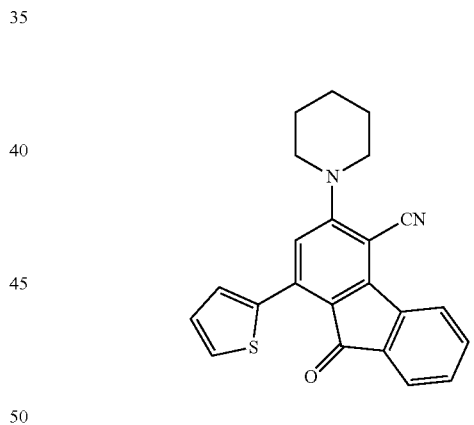

A solution of 3-(piperidin-1-yl)-1-(thiophen-2-yl)-9H-fluorene-4-carbonitrile (356 mg) in THF was added sodium hydride (38 mg) and was stirred at 0-5° C. for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Yellow solid; yield 89%; mp 172-174° C.; ESMS 371 (M$^+$+1); IR (KBr) 1703 cm$^{-1}$ (CO), 2218 (CN); $^1$H NMR (300 MHz, CDCl$_3$) δ 1.66-1.75 (m, 2H, CH$_2$), 1.81-1.90 (m, 4H, 2CH$_2$), 3.38-3.44 (m, 4H, 2CH$_2$), 6.88 (s, 1H, ArH), 7.18 (dd, J=8.85 Hz & J=3.75 Hz, 1H, ArH), 7.44 (t, J=7.5 Hz, 1H, ArH), 7.48 (d, J=6 Hz, 1H, CH), 7.59 (t, J=7.6 Hz, 1H, ArH), 7.68 (d, J=7.2 Hz, 1H, ArH), 7.84 (d, J=4.7 Hz, 1H, CH), 8.38 (d, J=7.5 Hz, 1H, CH).

51) 1-(4-Fluoro-phenyl)-9-oxo-3-piperidin-1-yl-9H-fluorene-4-carbonitrile

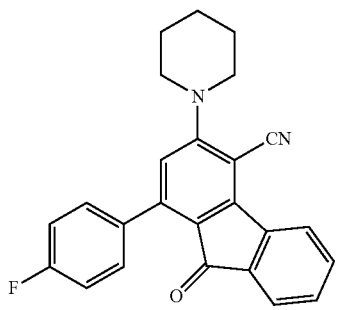 [SMILES: N#Cc1c(N2CCCCC2)cc(-c2ccc(F)cc2)c2c1-c1ccccc1C2=O]

A solution of 1-(4-fluorophenyl)-3-(piperidin-1-yl)-9H-fluorene-4-carbonitrile (368 mg) in THF was added sodium hydride (38 mg) and was stirred at room temperature for less than five minutes. After completion, the reaction solvent was evaporated under vacuum and the crude solid obtained was quenched with ice water and subsequently neutralized by dilute HCl. The precipitate thus obtained was filtered and purified on a silica gel column using ethyl acetate-hexane as eluent. Yellow solid; yield 91%; mp 180-182° C.; ESMS 383 (M$^+$+1); IR (KBr) 1707 cm$^{-1}$ (CO), 2219 (CN); $^1$H NMR (300 MHz, CDCl$_3$) δ 1.69-1.75 (m, 2H, CH$_2$), 1.80-1.89 (m, 4H, 2CH$_2$), 3.39-3.44 (m, 4H, 2CH$_2$), 6.63 (s, 1H, ArH), 7.16 (t, J=8.6 Hz, 2H, ArH), 7.41 (t, J=7.6 Hz, 1H, ArH), 7.46-7.53 (m, 2H, ArH), 7.56-7.65 (m, 2H, ArH), 8.37 (d, J=7.6 Hz, 1H, ArH).

We claim:

1. Donor-acceptor fluorene compounds, fluorenone compounds and their π-conjugated scaffolds having the general formula I, and derivatives thereof

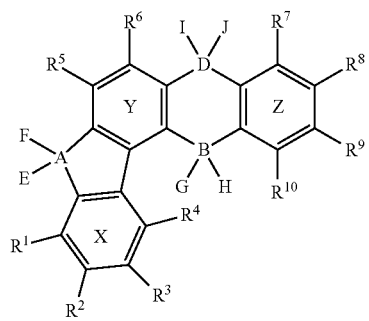

wherein R$^1$, R$^2$, R$^3$, R$^4$, R$^5$, R$^6$, R$^7$, R$^8$, R$^9$, and R$^{10}$ are independently selected, from the group consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, nitriles, esters, hydroxy, mercapto, carbontrifluoride, and nitro;

wherein A is selected from the group consisting of one carbon, optionally substituted one carbon unit, optionally a ketone group, an oxygen atom, and a sulfur atom;

B and D are selected from the units consisting of one carbon or two carbons, optionally substituted one carbon unit or substituted two carbon units, optionally a ketone group, optionally substituted alkene, an oxygen atom, and a sulfur atom;

wherein in A, B, and D units optionally either one unit is present, or optionally two units are present or optionally all three units are present, wherein unit B or D may be nothing and bond is directly linked to aromatic Y-Z benzene ring;

wherein units B, D and ring Z may not be present;

wherein E and F are selected from the group consisting of hydrogen, optionally substituted alkyl, optionally substituted alkenyl, optionally substituted alkoxyl, optionally substituted alkylthio, optionally substituted amino, optionally substituted acylamino, optionally substituted acylthio, optionally substituted acyl, optionally substituted acyloxy, optionally substituted thioamido, halogens, esters, hydroxy, mercapto, carbontrifluoride, and nitro;

wherein G, H, I, and J are selected from the group consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, and nitro; and wherein EF, GH or IJ together may be a double bond directly linked to an oxygen atom or a methylene group or optionally substituted methylene group;

wherein the compound is of the formula of Template T-1 to T-3 with the proviso that at least one donor group selected from the group consisting of pyrrolidine, piperidine, methyl amine, ethyl amine, propyl amine and dimethylamine and one acceptor group selected from the group consisting of nitriles and esters is present on these scaffolds;

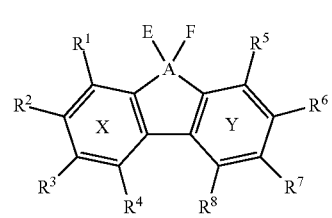

T-1

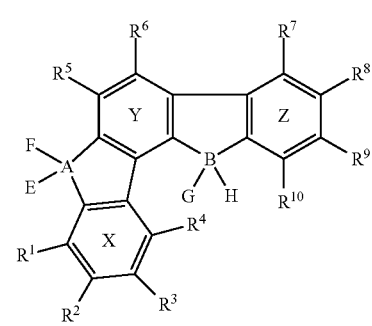

T-2

-continued

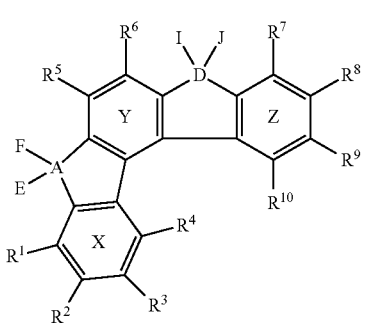

T-3 wherein in Template T-1, $R^1, R^2, R^3, R^4, R^5, R^6, R^7$, and $R^8$ are independently selected from the group consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, ester, hydroxy, mercapto, carbontrifluoride, and nitro;

wherein in Template T-1, A is selected from the units consisting of optionally substituted or unsubstituted one carbon unit, optionally a ketone group, an oxygen atom, and a sulfur atom;

wherein in Template T-1, E and/or F is selected from the group consisting of hydrogen, optionally substituted alkyl, optionally substituted alkenyl, optionally substituted alkoxyl, optionally substituted alkylthio, optionally substituted amino, optionally substituted acylamino, optionally substituted acylthio, optionally substituted acyl, optionally substituted acyloxy, optionally substituted thioamido, halogens, esters, hydroxy, mercapto, carbontrifluoride and nitro;

wherein in Template T-1, EF together may be a double bond directly linked to an oxygen atom or a methylene group or optionally substituted methylene group;

wherein in Template T-2, $R^1, R^2, R^3, R^4, R^5, R^6, R^7, R^8, R^9$, and $R^{10}$ are independently selected from the group consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally acylthio, optionally substituted acyl, optionally substituted aroyl, optionally substituted acyloxy, optionally substituted thioamido, halogens, esters, hydroxy, mercapto, carbontrifluoride and nitro;

wherein in Template T-2, A is selected from the group consisting of one carbon, optionally substituted one carbon unit, optionally a ketone group, an oxygen atom, and a sulfur atom; B is selected from the units consisting of one carbon or two carbons, optionally substituted carbon unit or substituted two carbon units, optionally a ketone group, optionally substituted alkene, an oxygen atom, and a sulfur atom;

wherein in Template T-2, E and F are selected from the group consisting of hydrogen, optionally substituted alkyl, optionally substituted alkenol, optionally substituted alkoxyl, optionally substituted alkylthio, optionally substituted amino, optionally substituted acylamino, optionally substituted acylthio, optionally substituted acyl, optionally substituted acyloxy, optionally substituted thioamido, halogens, esters, hydroxy, mercapto, carbontrifluoride, and nitro;

wherein in Template T-2, G, and H are selected from the group consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride and nitro;

wherein in Template T-2, EF and/or GH together may be a double bond directly linked to an oxygen atom or a methylene group or optionally substituted methylene group;

wherein in Template T-3, $R^1, R^2, R^3, R^4, R^5, R^6, R^7, R^8, R^9$, and $R^{10}$ are independently selected from the group consisting of hydrogen, optionally substituted alkyl, optionally substituted alkenyl, optionally substituted alkoxyl, optionally substituted aryl, optionally substituted heteroaryl, optionally Substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido halogens, esters, hydroxy, mercapto, carbontrifluoride and nitro;

wherein in Template T-3, A is selected from the group consisting of one carbon, optionally substituted one carbon unit, optionally a ketone group, an oxygen atom, and a sulfur atom; D is selected from the units consisting of one carbon or two carbons, optionally substituted one carbon unit or substituted two carbon units, optionally a ketone group, optionally substituted alkene, an oxygen atom, and a sulfur atom;

wherein in Template T-3, E and F are selected from the group consisting of hydrogen, optionally substituted alkyl, optionally substituted alkenyl, optionally substituted alkoxyl, optionally substituted alkylthio, optionally substituted amino, optionally substituted acylamino, optionally substituted acylthio, optionally substituted acyl, optionally substituted acyloxy, optionally substituted thioamido, halogens, esters, hydroxy, mercapto, carbontrifluoride, and nitro;

wherein in Template T-3, I, and J, are selected from the group consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, optionally substituted halogens, esters, hydroxy, mercapto, carbontrifluoride and nitro; and wherein in Template T-3, EF and/or IJ together may be a double bond directly linked to an oxygen atom or a methylene group or optionally substituted methylene group.

2. A compound as claimed in claim 1 selected from the group consisting of:

1) 1-Phenyl-3-pyrrolidin-1-yl-9H-fluorene-4-carbonitrile
2) 1-Phenyl-3-piperidin-1-yl-9H-fluorene-4-carbonitrile
3) 1-Naphthalen-1-yl-3-piperidin-1-yl-9H-fluorene-4-carbonitrile
4) 1-Naphthalen-2-yl-3-piperidin-1-yl-9H-fluorene-4-carbonitrile
5) 3-Piperidin-1-yl-1-pyren-1-yl-9H-fluorene-4-carbonitrile
6) 3,5-Dimethyl-furan-2-yl)-3-piperidin-1-yl-9H-fluorene-4-carbonitrile
7) 1-(4-Fluoro-phenyl)-3-piperidin-1-yl-9H-4-fluorene-4-carbonitrile
8) 3-Piperidin-1-yl-1-thiophen-2-yl-9H-fluorene-4-carbonitrile
9) 4-Furan-2-yl-2-piperidin-1-yl-9H-fluorene-1-carbonitrile
10) 4-Phenyl-2-pyrrolidin-1-yl-9H-fluorene-1-carbonitrile
11) 4-Phenyl-2-piperidin-1-yl-9H-fluorene-1-carbonitrile
12) 4-Naphthalen-1-yl-2-piperidin-1-yl-9H-fluorene-1-carbonitrile
13) 4-Naphthalen-2-yl-2-piperidin-1-yl-9H-fluorene-1-carbonitrile
14) 2-Piperidin-1-yl-4-pyren-1-yl-9H-fluorene-1-carbonitrile
15) 4-(4-Methoxy-phenyl)-2-piperidin-1-yl-9H-fluorene-1-carbonitrile
16) 2-Piperidin-1-yl-4-p-tolyl-9H-fluorene-1-carbonitrile
17) 4-(4-Chloro-phenyl)-2-pyrrolidin-1-yl-9H-fluorene-1-carbonitrile
18) 2-Pyrrolidin-1-yl-4-p-tolyl-9H-fluorene-1-carbonitrile
19) 2-Piperidin-1-yl-4-thiophen-2-yl-9H-fluorene-1-carbonitrile
20) 2-Piperidin-1-yl-4-(4-pyrrol-1-yl-phenyl)-9H-fluorene-1-carbonitrile
21) 4-(4-Acetyl-phenyl)-2-piperidin-1-yl-9H-fluorene-1-carbonitrile
22) 4-(4-Fluoro-phenyl)-2-piperidin-1-yl-9H-fluorene-1-carbonitrile
23) 4-(4-Bromo-phenyl)-2-piperidin-1-yl-9H-fluorene-1-carbonitrile
24) 6-Piperidin-1-yl-7,12-dihydro-indeno[1,2-a]fluorene-5-carbonitrile
25) 6-Pyrrolidin-1-yl-7,12-dihydro-indeno[1,2-a]fluorene-5-carbonitrile
26) 3-Methoxy-6-piperidin-1-yl-7,12-dihydro-indeno[1,2-a]fluorene-5-carbonitrile
27) 7-Piperidin-1-yl-5,8-dihydro-indeno[2,1-c]fluorene-6-carbonitrile
28) 7-Pyrrolidin-1-yl-5,8-dihydro-indeno[2,1-c]fluorene-6-carbonitrile
29) (4-Methyl-piperidin-1-yl)-5,8-dihydro-indeno[2,1-c]fluorene-6-carbonitrile
30) 11-Methoxy-7-piperidin-1-yl-5,8-dihydro-indeno[2,1-c]fluorene-6-carbonitrile
31) 7-(Piperidin-1-yl)-6,9-dihydro-5H-indeno[2,1-c]phenanthrene-8-carbonitrile
32) 7-(Pyrrolidin-1-yl)-6,9-dihydro-5H-indeno[2,1-c]phenanthrene-8-carbonitrile
33) 7-(4-Methyl-piperidin-1-yl)-6,9-dihydro-5H-indeno[2,1-c]phenanthrene-8-carbonitrile
34) 9-Oxo-4-phenyl-2-pyrrolidin-1-yl-9H-fluorene-1-carbonitrile
35) 9-Oxo-4-phenyl-2-piperidin-1-yl-9H-fluorene-1-carbonitrile
36) 4-Naphthalen-1-yl-9-oxo-2-piperidin-1-yl-9H-fluorene-1-carbonitrile
37) 4-Naphthalen-2-yl-9-oxo-2-piperidin-1-yl-9H-fluorene-1-carbonitrile
38) 9-Oxo-2-piperidin-1-yl-4-pyren-1-yl-9H-fluorene-1-carbonitrile
39) 9-Oxo-2-piperidin-1-yl-4-thiophen-2-yl-9H-fluorene-1-carbonitrile
40) 4-Furan-2-yl-2-piperidin-1-yl-9H-fluorene-1-carbonitrile
41) 4-(4-Methoxy-phenyl)-9-oxo-2-piperidin-1-yl-9H-fluorene-1-carbonitrile
42) 4-(4-Fluoro-phenyl)-9-oxo-2-piperidin-1-yl-9H-fluorene-1-carbonitrile
43) 9-Oxo-2-piperidin-1-yl-4-p-tolyl-9H-fluorene-1-carbonitrile
44) 9-oxo-2-pyrrolidin-1-yl-4-p-tolyl-9H-fluorene-1-carbonitrile
45) 9-Oxo-1-phenyl-3-pyrrolidin-1-yl-9H-fluorene-4-carbonitrile
46) 9-Oxo-1-phenyl-3-piperidin-1-yl-9H-fluorene-4-carbonitrile
47) 1-Naphthalen-1-yl-9-oxo-3-piperidin-1-yl-9H-fluorene-4-carbonitrile
48) 1-Naphthalen-2-yl-9-oxo-3-piperidin-1-yl-9H-fluorene-4-carbonitrile
49) 9-Oxo-3-piperidin-1-yl-1-pyren-1-yl-9H-fluorene-4-carbonitrile
50) 9-Oxo-3-piperidin-1-yl-1-thiophen-2-yl-9H-fluorene-4-carbonitrile and
51) 1-(4-Fluoro-phenyl)-9-oxo-3-piperidin-1-yl-9H-fluorene-4-carbonitrile.

3. A compound as claimed in claim 1, wherein the compound is useful for the preparation of electroluminescent devices such as organic light emitting diodes, a photodetector, and a photovoltaic device and other useful electronic devices and with high brightness and efficiency.

4. A compound as claimed in claim 1, wherein these compounds can be used alone or in combination with filters to produce any desired colored light from full color spectrum as per the requirement of the color including white light.

5. An electronic device comprising one or a plurality of layers disposed between two electrical contact layers such that at least one of the layers includes fluorenes and their pi-conjugated scaffolds having general formula I or fluorenones and their pi-conjugated scaffolds having general formula I or derivatives thereof as claimed in claim 1.

6. A device as claimed in claim 5, wherein the device comprises of at least a photo active layer disposed between the said electrical contact layers, such that the photo active layer includes fluorenes and their pi-conjugated scaffolds having general formula I or fluorenone and their pi-conjugated scaffolds having general formula I or derivatives thereof.

7. A device as claimed in claim 5, wherein the device comprises of at least an electro active layer disposed between the said electrical contact layers, such that the electro active layer includes fluorenes and their pi-conjugated scaffolds having general formula I of fluorenone and their pi-conjugated scaffolds having general formula I or derivatives thereof.

8. A device as claimed in claim 5, wherein the device comprises of at least a hole injection and or transparent layer disposed between the said electrical contact layers, such that the hole injection layer and or transport layer includes fluorenes and their pi-conjugated scaffolds having general formula I or fluorenone and their pi-conjugated scaffolds having general formula I or derivatives thereof.

9. A device as claimed in claim 5, wherein the device comprises of at least an electron injection and or transport layer disposed between the said electrical contact layers, such that the electron injection and or transport layer includes fluorenes and their pi-conjugated scaffolds having general formula I or fluorenone and their pi-conjugated scaffolds having general formula I or derivatives thereof.

10. A compound of claim 1 wherein E and F are each hydrogens, or E and F together may be a double bond directly linked to an oxygen atom.

11. A process for the preparation of donor-acceptor fluorenes, and fluorenones of the general formula 1 comprising the process of preparation of template T-1 or template T-2 or template T-3 as claimed in claim 1 comprising the steps of:
  a. Reacting a compound having general formula S-1 with a compound having general formula S-2 to furnish a compound having the general formula T-1
    wherein $R^1$, $R^2$, $R^3$, $R^4$, $R^5$, $R^6$, $R^7$, and $R^8$ are independently selected from the group consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride and nitro;
    wherein A is selected from the units consisting of optionally substituted or unsubstituted one carbon unit, optionally a ketone group, an oxygen atom, and a sulfur atom;
    wherein E and/or F is selected from the group consisting of hydrogen, optionally substituted alkyl, optionally substituted alkenyl, optionally substituted alkoxyl, optionally substituted alkylthio, optionally substituted amino, optionally substituted acylamino, optionally substituted acylthio, optionally substituted acyl, optionally substituted aroyl, optionally substituted acyloxy, optionally substituted thioamido, halogens, esters, hydroxy, mercapto, carbontrifluoride and nitro;
    wherein EF together may be a double bond directly linked to an oxygen atom or a methylene group or optionally substituted methylene group;

Synthesis of Template T-1

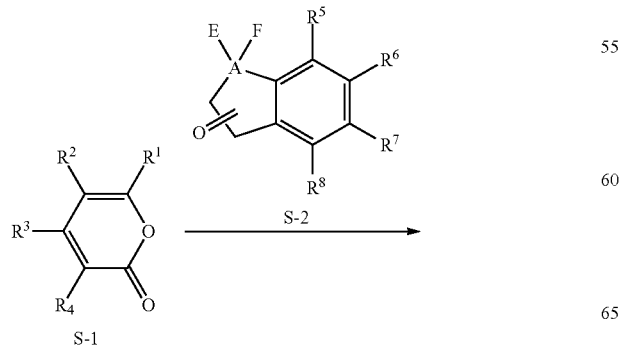

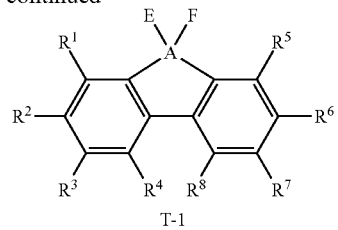

or reacting a compound having general formula S-3 with a compound having general formula S-4 to furnish a compound having the general formula T-2
  wherein $R^1$, $R^2$, $R^3$, $R^4$, $R^5$, $R^6$, $R^7$, $R^8$, $R^9$, and $R^{10}$ are independently selected from the group consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acyithio, optionally substituted acyl, optionally substituted aroyl, optionally substituted acyloxy, optionally substituted thioamido, halogens, esters, hydroxy, mercapto, carbontrifluoride and nitro;
  wherein A is selected from the units consisting of optionally substituted or unsubstituted one carbon unit, optionally a ketone group, an oxygen atom, and a sulfur atom;
  B is selected from the units consisting of one carbon or two carbons, optionally substituted one carbon unit or substituted two carbon units, optionally a ketone group, optionally substituted alkene, an oxygen atom, and a sulfur atom;
  wherein E and F are selected from the group consisting of hydrogen, optionally substituted alkyl, optionally substituted alkenyl, optionally substituted alkoxyl, optionally substituted alkylthio, optionally substituted amino, optionally substituted acylamino, optionally substituted acylthio, optionally substituted acyl, optionally substituted acyloxy, optionally substituted thioamido, halogens, esters, hydroxy, mercapto, carbontrifluoride, and nitro;
  wherein G and H are selected from the group consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, and nitro;
  wherein EF or GH together may be a double bond directly linked to an oxygen atom or a methylene group or optionally substituted methylene group;

Synthesis of Template T-2

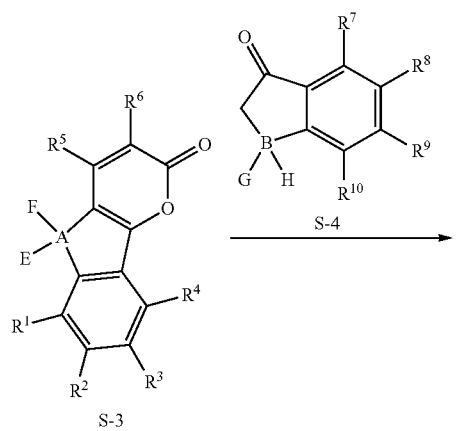

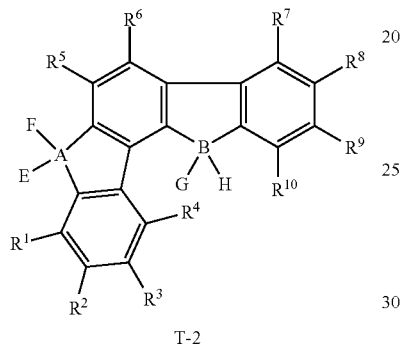

or reacting a compound having general formula S-3 with a compound having general formula S-5 to furnish a compound having the general formula T-3 wherein $R^1$, $R^2$, $R^3$, $R^4$, $R^5$, $R^6$, $R^7$, $R^8$, $R^9$, and $R^{10}$ are independently, selected from the group consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride and nitro;

wherein A is selected from the units consisting of optionally substituted or unsubstituted one carbon unit, optionally a ketone group, an oxygen atom, and a sulfur atom;

D is selected from the units consisting of one carbon or two carbons, optionally substituted one carbon unit or substituted two carbon units, optionally a ketone group, optionally substituted alkene, an oxygen atom, and a sulfur atom;

wherein E and F are selected from the group consisting of hydrogen, optionally substituted alkyl, optionally substituted alkenyl, optionally substituted alkoxyl, optionally substituted alkylthio, optionally substituted amino, optionally substituted acylamino, optionally substituted acylthio, optionally substituted acyl, optionally substituted acyloxy, optionally substituted thioamido, halogens, esters, hydroxy, mercapto, carbontrifluoride, and nitro;

wherein I and J are selected from the group consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, and nitro;

wherein EF or GH together may be a double bond directly linked to an oxygen atom or a methylene group or optionally substituted methylene group;

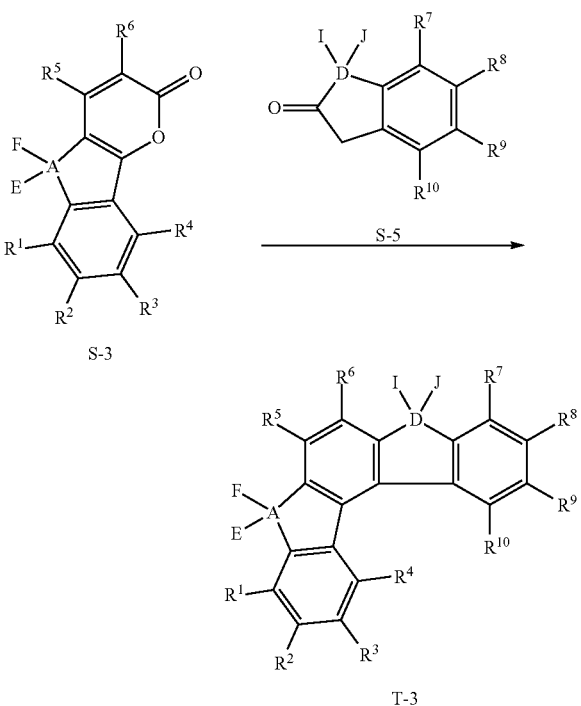

in an organic solvent in the presence of a base at a temperature ranging between −78° C. to 100° C. for a period ranging between <1 minute to 24 hours, b. isolating the compound of general formula T-1, T-2, T-3 from the reaction mixture obtained in step a respectively and purifying by chromatographic techniques, and c. oxidizing the fluorene templates T-1, T-2, T-3 to a corresponding fluorenone or diaryl carbonyl compounds by treating the fluorenone or related diarylmethane compounds with an oxidizing agent in the presence of an alkali metal hydride or alkaline earth metal hydrides in an organic solvent for a time sufficient and at a temperature ranging from −78° C. to 100° C. sufficient to convert the fluorene or related diarylmethane compounds to the fluorenone or diaryl carbonyl compounds.

12. A compound selected from the group consisting of 3-piperidin-1-yl-1-pyren-1-yl-9H-fluorene-4-carbonitrile and 2-piperidin-1-yl-4-pyren-1-yl-9H-fluorene-1-carbonitrile.

* * * * *